US006458801B1

(12) United States Patent
Carniato et al.

(10) Patent No.: US 6,458,801 B1
(45) Date of Patent: Oct. 1, 2002

(54) BENZOFURANE DERIVATIVES, PREPARATION METHOD, USE AS MEDICINES AND PHARMACEUTICAL COMPOSITIONS CONTAINING SAME

(75) Inventors: Denis Carniato, Cagnes sur Mer (FR); Thomas R. Gadek, Oakland, CA (US); Jean-Francois Gourvest, Claye-Souilly (FR); Jochen Knolle, Kriftel (DE); Anurschirwan Peyman, Kelkheim (DE); Sarah C. Bodary, San Bruno, CA (US)

(73) Assignees: Aventis Pharma S.A. (FR); Genentech, Inc.

( * ) Notice: Subject to any disclaimer, the term of this patent is extended or adjusted under 35 U.S.C. 154(b) by 0 days.

(21) Appl. No.: 09/856,542

(22) PCT Filed: Nov. 23, 1999

(86) PCT No.: PCT/FR99/02879

§ 371 (c)(1),
(2), (4) Date: Jun. 9, 2001

(87) PCT Pub. No.: WO00/31070

PCT Pub. Date: Jun. 2, 2000

(30) Foreign Application Priority Data

Nov. 23, 1999 (FR) .............................................. 9814779

(51) Int. Cl.⁷ ........................ A61K 31/505; A61K 31/34
(52) U.S. Cl. ........................ 514/275; 514/469; 549/441; 549/331
(58) Field of Search ................................ 514/275, 469; 544/331; 549/441

(56) References Cited

FOREIGN PATENT DOCUMENTS

| WO | 9408962 | 4/1994 |
| WO | 9532710 | 12/1995 |
| WO | 0820991 | 1/1998 |

*Primary Examiner*—Amelia Owens
(74) *Attorney, Agent, or Firm*—Bierman, Muserlian and Lucas

(57) ABSTRACT

A compound of the formula

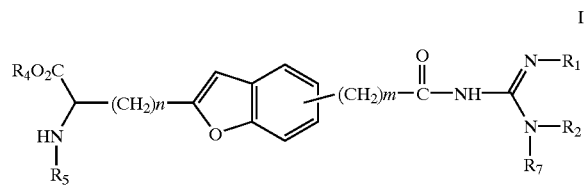

wherein the substituents are as defined in the specification and its pharmaceutically acceptable salts and its prodrug useful for treating osteoporosis.

14 Claims, No Drawings

BENZOFURANE DERIVATIVES, PREPARATION METHOD, USE AS MEDICINES AND PHARMACEUTICAL COMPOSITIONS CONTAINING SAME

This application is a 371 of PCT/FR99/02879 filed Nov. 23, 1999.

A subject of the present invention is new benzofurane derivatives, their preparation process, their use as medicaments and the pharmaceutical compositions containing them.

A subject of the invention is the compounds of formula (I)

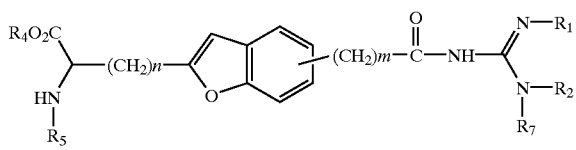

in which $R_1$, $R_2$, $R_4$, $R_5$ and $R_7$ have the meanings indicated below, their physiologically acceptable salts and their prodrugs. The compounds of formula (I) are compounds having a pharmacological activity and can therefore be used as medicaments. They are antagonists of the vitronectin receptor and cell adhesion inhibitors and they inhibit bone resorption mediated by the osteoclasts. They are therefore useful for the therapeutic or prophylactic treatment of diseases which are caused at least in part to an undesirable increase in bone resorption, for example osteoporosis. A subject of the invention is also the processes for preparation the compounds of formula (I), their use, in particular as a medicament, and the pharmaceutical compositions containing them. The bone is constantly subjected to a dynamic process which includes bone resorption and bone formation. These processes are mediated via specialized cells. Bone formation is the result of the deposit of a mineral matrix by the osteoblasts and bone resorption is the result of the dissolution of this bone matrix by the osteoclasts. The majority of bone disorders are caused by a disturbed equilibrium between bone formation and bone resorption. Osteoporosis is characterized by a dry loss of this bone matrix. An activated mature osteoclast resorbs the bone after adhesion to the bone matrix via the secretion of proteolytic enzyme, and protons inside the adhesion zone, resulting in depressions or hollows on the bone surface which appear when the osteoclast detaches itself from the bone. Studies have shown that the fixation of the osteoclast on the bone is mediated by receptors: the integrins. Integrins are a superfamily of receptors mediating the cell/cell and more particularly cell/matrix adhesion process, including in particular $\alpha_{IIb}\beta_3$ as a blood platelet receptor (fibrinogen) and $\alpha_v\beta_3$ as vitronectin receptor. The peptides containing the RGD unit as well as the anti $\alpha_v\beta_3$ antibodies are known for their ability to inhibit resorbtion of dentin and prevention of osteoclast adhesion on the mineralized matrices (Horton et al. Exp. Cell. Res. (1991), 195, 368). The peptide Echistatine, isolated from snake venom also contains an RGD unit and is described as an inhibitor of the adhesion of osteoclasts to the bone and is a powerful inhibitor of bone resorption in tissues cultured in vitro (Sato et al. J. Cell. Biol. (1990), 111, 1713) and in vivo in the rat (Fisher et al. Endocrinology (1993), 132, 1411). The $\alpha_v\beta_3$ receptor is a transmembrane glycoprotein which is expressed in a large number of cells including endothelial cells, smooth muscle cells, osteoclast and cancerous cells which thus leads to a pluripotentiality of the compounds of formula (I) according to the invention.

In fact, the $\alpha_v\beta_3$ receptors expressed in the membrane of the osteoclasts are the basis of the adhesion/resorption process, contribute to the organization of the cell cytoskeleton, and are involved in osteoporosis. The $\alpha_v\beta_3$ receptors expressed in the smooth muscle cells of the aorta, stimulate their migration towards the neointima, which leads to the formation of arteriosclerosis and the occurrence of post-angioplastic recurrence of stenosis (Brown et al., cardiovascular Res. (1994), 28, 1815).

The endothelial cells secrete growth factors which are mitogens for the endothelium and can contribute to the formation of new blood vessels (Angiogenesis). The antagonists of $\alpha_v\beta_3$ integrin can therefore lead to a regression of cancerous tumors by inducing apoptosis of the angiogenic blood vessels. (Brook et al. Cell (1994) 79, 1157). Cheresh et al (Science 1995, 270, 1500) have described anti-$\alpha_v\beta_3$ antibodies or antagonists of the $\alpha_v\beta_3$ receptor which inhibit the process of angiogenesis induced by bFGF in the rat eye, a property which can be used for the treatment of retinopathies, in particular in diabetics. The Patent Application WO-A-94/12181 describes aromatic or non-aromatic substituted systems and WO-A-94/08577 describes substituted heterocycles as antagonists of the fibrinogen receptor and inhibitors of platelet aggregation. EP-A-528586 and EP-A-528587 describe phenylalanine derivatives substituted by an aminoalkyl or a heterocycle and WO-A-95/32710 describes aryl derivatives as inhibitors of bone resorption by the osteoclasts. WO-A-96/00574 describes benzodiazepines and WO-A-96/00730 describes compounds which inhibit the fibrinogen receptor, in particular benzodiazepines which are linked to a ring with 5 nitrogenous members as antagonists of the vitronectin receptor. DE-A-19654483 describes tyrosine derived antagonists of the vitronectin receptor. DE-A-19629816.4 claims cycloalkyl derivatives as antagonists of the vitronectin receptor. Other investigations have made it possible to show that the acylguanidine derivatives of formula (I) show marked activity as inhibitors of the vitronectin receptor and of bone resorption mediated via the osteoclasts.

A subject of the invention is the compounds of formula (I)

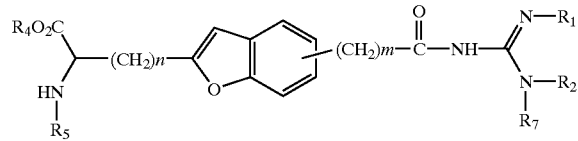

in which
either $R_1$ and $R_2$, independently of each other, represent a hydrogen atom or an alkyl group containing 1 to 6 carbon atoms non-substituted or substituted by $R_3$,
or $R_1$ and $R_2$ form together a divalent alkylene radical containing 2 to 9 carbon atoms, saturated or unsaturated, such as $-(CH_2)_p-$ in which p is 2, 3, 4, 5, 6, 7, 8 or 9, non-substituted or substituted by one or more radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl, $(C_3-C_{12})$-cycloalkyl-$(C_1-C_6)$-alkyl and oxo, said divalent alkylene radical being able to be attached at the level of the carbon-carbon bond to a carbocycle or heterocycle with 5 to 7 members, containing 1 or 2 atoms of nitrogen, saturated or unsaturated, non-substituted or substituted by 1 or 2 $R_3$ radicals $R_3$ represents a $(C_1–C_8)$-alkyl, $(C_1–C_8)$-alkoxy, $(C_5–C_{14})$-aryl, $(C_5–C_{14})$-aryl-$(C_1–C_4)$-alkyl, halogen, trifluoromethyl, hydroxyl, nitro, amino, NH—$((C_1–C_4)$-alkyl), $N((C_1–C_4)alkyl)_2$, NHCO—$(C_1–C_4)$-alkyl or CO—$(C_1–C_4)$alkyl group;

$R_4$ represents
  either a hydrogen atom,
  or a $(C_1–C_6)$-alkyl-CO—O—$(C_1–C_4)$-alkyl or $(C_1–C_6)$-alkyl group, non-substituted or substituted by a radical chosen from hydroxyl, $(C_1–C_4)$-alkoxy, $(C_1–C_4)$-alkyl-$SO_2$, $NR_9R_9'$ and $N^+R_9R_9'R_9''Q^-$, in which $R_9$, $R_9'$ and $R_9''$ independently from one another, represent a hydrogen, a $(C_1–C_6)$-alkyl, $(C_5–C_{14})$-aryl or $(C_5–C_{14})$-aryl-$(C_1–C_4)$-alkyl group and $Q^-$ is a physiologically acceptable anion,
  or one of the following radicals:

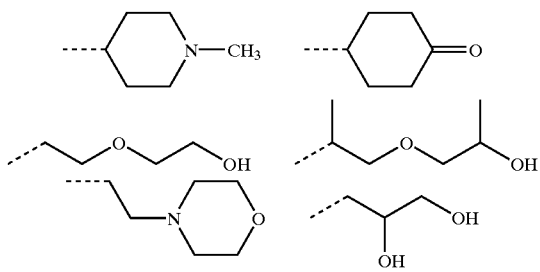

the dotted lines representing the position of the bond;

$R_5$ represents a hydrogen atom or a group chosen from $COR_6$, $CO_2R_6$, $SO_2R_6$, $SO_2NHR_6$, $SO_2NHCOR_6$, $SO_2NHCO_2R_6$, $CONH_2$ and $CONHR_6$ in which $R_6$ represents $(C_1–C_8)$-alkyl, $(C_6–C_{14})$-aryl, $(C_6–C_{14})$-aryl-$(C_1–C_6)$-alkyl, $(C_5–C_{14})$-heteroaryl or $(C_5–C_{14})$-heteroaryl-$(C_1–C_6)$-alkyl, $(C_3–C_{20})$(mono-, bi- or tri-)-cycloalkyl, $(C_3–C_{20})$(mono-, bi- or tri-)-cycloalkyl-$(C_1–C_6)$alkyl, the aryl or heteroaryl radical being non-substituted or substituted by 1, 2 or 3 $R_3$ radicals;

$R_7$ represents a hydrogen atom, $(C_1–C_6)$-alkyl-O—CO—, hydroxyl, $(C_1–C_6)$-alkyl-O—CO—O— or nitro;

m is equal to 0, 1, 2 or 3;

n is an integer equal to 1, 2 or 3;

said compounds of formula (I) being in all their possible isomer forms, alone or in a mixture in any ratio, the acylguanidine group adjacent to the phenyl being in para or meta position of the oxygen, as well as their physiologically acceptable salts and their prodrugs.

All the radicals which can be found several times in the compounds of formula (I), for example the $R_3$ radical, are independent from one another and can be identical or different.

The alkyl radicals can be linear or branched, saturated or mono- or polyunsaturated. This also applies when they carry a substituent or when they are included in groups such as for example alkoxy, alkoxycarbonyl, aralkyl or heteroarylalkyl. By $(C_1–C_8)$-alkyl is meant the methyl, ethyl, propyl, butyl, pentyl, hexyl, heptyl, octyl, nonyl radicals, the n-isomers of these radicals, isopropyl, isobutyl, isopentyl, neopentyl, isohexyl, 3-methylpentyl, 2,3,4-trimethylhexyl, sec-butyl, tert-butyl, tert-pentyl. Among the preferred radicals methyl, ethyl, n-propyl, isopropyl, n-butyl, isobutyl, and tert-butyl can be mentioned.

The divalent alkylene radicals corresponding to the monovalent radicals mentioned above are for example the methylene, ethylene, 1,3-propylene, 1,2-propylene (=1-methylethylene), 2,3-butylene (=1,2-dimethylethylene), 1,4-butylene or 1,6-hexylene radicals. The unsaturated alkyl radicals are for example the alkenyl radicals such as vinyl, 1-propenyl, allyl, butenyl, 3-methyl-2-butenyl or the alkynyl radicals such as ethynyl, 1-propynyl or propargyl.

By unsaturated divalent alkylene radicals is meant the alkenylene and alkynylene radicals which can also be linear or branched. They are for example vinylene, propenylene, ethynylene or propynylene radicals.

The cycloalkyl radicals can be monocyclic, bicyclic or tricyclic. They are for example cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl which if appropriate can be substituted for example by an alkyl containing 1 to 4 carbon atoms. As substituted cycloalkyl radicals, there can be mentioned 4-methylcyclohexyl and 2,3-dimethylcyclohexyl.

The bicycloalkyl and tricycloalkyl radicals can be non-substituted or substituted in any position, for example by one or more oxo groups and/or 1 or more identical or different alkyl groups such as methyl or isopropyl and preferably methyl. The junction bond of the bi or tricyclic radical can be situated in all positions of the molecule. The bond can be situated at the bridged carbon atom or of one of the other carbon atoms. This bond can also take any position from the point of view of the stereochemistry, for example exo or endo. As examples of bicycloalkyl or tricycloalkyl radicals, there can be mentioned camphanyl, bornyl, adamantyl such as 1-adamantyl or 2-adamantyl, caranyl, epii-sobornyl, epibornyl, norbornyl or norpinanyl.

By halogen is meant fluorine, chlorine, bromine or iodine.

By the term $(C_5–C_{14})$-aryl is meant
  either the heterocyclic $(C_5–C_{14})$-aryl radicals $(=(C_5–C_{14})$-heteroaryl), in which the carbon atoms of the ring are replaced with a heteroatom such as nitrogen, oxygen or sulphur,
  or the carbocyclic $(C_6–C_{14})$-aryl radicals.

Among the carbocyclic $(C_6–C_{14})$-aryl radicals, phenyl, naphthyl, biphenylyl, anthryl or fluorenyl and quite particularly 1-naphthyl, 2-naphthyl and phenyl can be mentioned.

Unless indicated to the contrary, the aryl radicals, in particular phenyl, can be non-substituted or substituted by one or more identical or different radicals chosen from $(C_1–C_8)$-alkyl, in particular $(C_1–C_4)$alkyl, $(C_1–C_8)$-alkoxy, halogen such as fluorine, chlorine and bromine, nitro, amino, trifluoromethyl, hydroxyl, methylenedioxy, cyano, hydroxycarbonyl, aminocarbonyl, $(C_1–C_4)$-alkoxycarbonyl, phenyl, phenoxy, benzyl and benzyloxy. In general, up to 2 nitro groups can be used in the compounds of formula (I) according to the invention.

In the case of monosubstituted phenyl, the substituent can be situated in position 2, 3 or 4, and preferably in position 3 or 4. In the case where the phenyl is disubstituted, the substituents can be in position 2, 3 or 2, 4 or 2, 5 or 2, 6 or 3, 4 or 3, 5. Preferably, in the disubstituted phenyls, the two substituents are in position 3,4. When this phenyl is trisubstituted, the positions are as follows: 2, 3, 4 or 2, 3, 5 or 2, 3, 6 or 2, 4, 5 or 2, 4, 6 or 3, 4, 5. In the same way, the naphthyl radicals or other aryl radicals can be substituted in any position, for example the 1-naphthyl radical in position 2-, 3-, 4-, 5-, 6-, 7-, and 8 and the 2-naphthyl radical in position 1-, 3-, 4-, 5-, 6-, and 7.

The $(C_5–C_{14})$-aryl group can also represent a monocyclic or polycyclic aromatic system in which 1, 2, 3, 4 or 5 carbon atoms of the ring are replaced with heteroatoms, in particular identical or different from the group constituted by nitrogen, oxygen and sulphur. Among the heterocyclic $(C_5–C_{14})$-aryl (=$(C_5-C_{14})$-heteroaryl) groups there can be mentioned the 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl groups or also benzocondensed, cyclopenta-cyclohexa- or cyclohepta-condensed derivatives of these radicals. The heterocyclic system can be substituted by the same substituents mentioned above for the carbocyclic system.

Among the heteroaryl radicals, the monocyclic or bicyclic aromatic systems having 1, 2 or 3 heteroatoms are preferred, in particular having 1 or 2 heteroatoms, chosen from N, O or S, and which are non-substituted or substituted by groups such as $(C_1-C_6)$-alkyl, $(C_1-C_6)$-alkoxy, fluorine, chlorine, nitro, amino, trifluoromethyl, hydroxyl, $(C_1-C_4)$-alkoxycarbonyl, phenyl, phenoxy, benzyloxy and benzyl. Quite particularly, there can be mentioned the monocyclic or bicyclic aromatic systems containing 5 to 10 members having 1 to 3 heteroatoms, in particular 1 or 2 heteroatoms, chosen from N, O and S and which can be substituted by 1 or 2 substituents such as $(C_1-C_4)$-alkyl, $(C_1-C_4)$-alkoxy, phenyl, phenoxy, benzyl and benzyloxy.

When $R_1$ and $R_2$ together form a divalent alkylene radical containing 2 to 9 carbon atoms, $R_1$ and $R_2$ form together with the two nitrogen atoms to which they are linked and the central carbon atom of the guanidine to which the two nitrogen atoms are linked, a monocyclic 1,3-diazaheterocycle which is linked to the nitrogen atom in the $(CH_2)m$—CO—NH group via its position 2.

As an example of 1,3-heterocycles which can be substituted as indicated at the level of the $(C_2-C_9)$-alkylene radical or of the nitrogen atom of the guanidine, there can be mentioned the 2-imidazolyl radical, the 4,5-dihydro-2-imidazolyl radical, the 1,4,5,6-tetrahydro-2-pyrimidinyl radical or the 4,5,6,7-tetrahydro-1H-1,3-diazepin-2-yl radical.

In the case where a ring with 5 to 7 members is condensed at the level of the carbon-carbon bond of the $(C_2-C_9)$-alkylene radical, then $R_1$ and $R_2$ form together with the two nitrogen atoms to which they are linked and the central carbon atom of the guanidine to which the two nitrogen atoms are linked, a bicyclic heterocycle which is linked to the nitrogen atom of the $(CH_2)m$—CO—NH group and which can be substituted as indicated above.

The rings with 5 to 7 members condensed at the level of the carbon-carbon bond of the $(C_2-C_9)$-alkylene radical can be saturated, mono-unsaturated, di-unsaturated or aromatic; they can be for example cycopropane, cyclohexane, cyclohexene, cyclohexadiene, cycloheptane or benzene.

Among the bicyclic aromatic sytems linked to the nitrogen atom of the $(CH_2)m$—CO—NH group the 1,3a,4,5,6,6a-hexahydro-1,3-diazapentalen-2-yl radical, the 1H-2-benzimidazolyl radical, the 3a,4,5,6,7,7a-hexahydro-1H-benzymidazol-2-yl radical, the 4,5,6,7-tetrahydro-1H-benzimidazol-2-yl radical, the 4,7-dihydro-1H-benzyimidazole-2-yl radical or the 1H-imidazo[4,5-b]pyridin-2-yl radical can be mentioned.

In the case where the condensed ring is substituted and/or the $(C_2-C_9)$-alkylene radical is substituted, they are preferably mono- or di-substituted independently from one another by an identical or different $R_3$ radical. In the case where $R_7$ and/or $R_2$ are substituted alkyl groups, they are preferably mono- or di-substituted independently from one another by an identical or different $R_3$ radical. The optically active carbon atoms contained in the compounds of formula (I) can independently from one another show n the R configuration or the S configuration. The compounds of formula (I) can be in the form of pure enantiomers or pure diastereoisomers or in the form of a mixture of enantiomers, for example in the form of racemates or mixtures of diastereoisomers.

A subject of the present invention is therefore pure enantiomers, mixtures of these enantiomers, pure diastereoisomers and mixtures of these diastereoisomers.

The invention relates to mixtures of two or more than two stereoisomers of formula (I) and all the ratios of these stereoisomers in said mixtures.

The compounds of formula (I) can, if appropriate, be present in the form of E isomers or Z isomers. A subject of the invention is therefore the pure E isomers, the pure Z isomers and the E/Z mixtures in any ratio.

The invention also relates to all the tautomer forms of the compounds of formula (I), realting for example to the form represented by formula (I), the form in which acylguanidine is present in the form of a —CO—N=C(NHR$_1$)—NR$_2$R$_7$ group, and all the other forms which differ by the different position of the hydrogen atom are considered.

Finally the invention relates to the different regioisomers linked to the para or meta position of the $(CH_2)_m$—CONH—C(=NR$_1$)(NR$_2$R$_7$) group with respect to the oxygen of the benzofurane. The diastereoisomers, including the E/Z isomers, can be separated into individual isomers, for example by chromatography. The racemates can be separated into two enantiomers by standard methods such as chiral phase chromatography or by resolution methods.

The physiologically acceptable salts of the compounds of formula (I) are in particular salts which can be used pharmaceutically or non-toxic salts or salts which can be used physiologically.

When the compounds of formula (I) contain an acid group such as carboxylic, they are for example salts of alkali or alkaline earth metals such as sodium, potassium, magnesium, calcium salts, and also the salts formed with physiologically acceptable quaternary ammonium ions and the addition salts with acids such as ammonia and physiologically acceptable organic amines such as for example triethylamine, ethanolamine or tris-(2-hydroxyethyl)amine.

When the compounds of formula (I) contain a basic group, they can form an addition salt with acids, for example with inorganic acids such as hydrochloric, sulphuric, phosphoric acid or with organic carboxylic acids such as acetic, trifluoroacetic, citric, benzoic, maleic, fumaric, tartaric, methanesulphonic or para toluene sulphonic acid.

The compounds of formula (I) which comprise a basic group and an acid group, such as for example guanidino and carboxylic, can be present in the form of Zwiterions (betaines), which are also included in the present invention. The physiologically acceptable Q$^-$ anion which is contained in the compounds of formula (I) when $R_4$ is an alkyl radical substituted by a charged ammonium group, is preferably a monovalent anion or an equivalent of a polyvalent anion of an organic or inorganic non-toxic, physiologically acceptable and in particular pharmaceutically acceptable acid, for example the anion or an anion equivalent of one of the acids mentioned above which can be used for the formation of the addition salts. Q$^-$ can be for example one of the anions (or anion equivalent) of a group chosen from chlorine, sulphate, phosphate, acetate, trifluoroacetate, citrate, benzoate, maleate, fumarate, tartrate, methanesulphonate and para-toluenesulphonate.

The salts of the compounds of formula (I) can be obtained by standard methods known to a person skilled in the art, for example by combining a compound of formula (I) with an organic or inorganic acid or a base in a solvent or a dispersant or from another salt by cation or anion exchange.

The invention also includes all the salts of the compounds of formula (I) which, because of their low physiological acceptability, cannot be used directly as medicaments, but can be used as intermediate products to implement subsequent chemical modifications in the compounds of formula (I) or as starting products for the preparation of physiologically acceptable salts.

The present invention also includes all the solvates of the compounds of formula (I) for example the hydrates, the solvates formed with alcohols, and all the derivatives of the compounds of formula (I), for example the esters, prodrugs and other physiologically acceptable derivatives, as well as the metabolites of the compounds of formula (I).

A more particular subject of the invention is the prodrugs of the compounds of formula (I) which can be converted to compounds of formula (I) in vivo under physiological conditions. The prodrugs of the compounds of formula (I), namely the chemically modified derivatives of the compounds of formula (I) are known to a person skilled in the art in order to obtain the improved properties in a desired fashion.

For more information on the type of prodrug envisaged in the present invention, the following books can be mentioned: Fleicher et al., Advanced Drug Delivery Review 19 (1996) 115–130; Design of prodrugs, H. Bundgaard, Ed., Elsevier, 1985; H. Bungaard, Drugs of the Future 16 (1991) 443; Saulnier et al. Bioorg. Med. Chem. Lett. 4 (1994) 1985; Safadi et al. Pharmaceutical Res. 10 (1993) 1350. Among the different appropriate prodrugs of the compounds of formula (I) there can preferably be mentioned:

prodrugs in the form of esters of the carboxylic groups, in particular of the COOH group, which is present when $R_4$ in $COOR_4$ is a hydrogen atom prodrugs in the form of acyl and carbamate for the groups containing an acylable nitrogen such as the amino groups and in particular guanidine. In the acylated prodrugs or in the form of carbamate, one or more times, for example twice, a hydrogen atom situated on the nitrogen atom is replaced with an acyl or carbamate group. Among the preferred acyl or carbamate groups, there can be mentioned the $R_{10}CO$—, $R_{11}OCO$-groups, in which $R_{10}$ is a hydrogen, $(C_1-C_{18})$-alkyl, $(C_3-C_{14})$-cycloalkyl, $(C_3-C_{14})$cycloalkyl-$(C_1-C_8)$-alkyl, $(C_5-C_{14})$-aryl, in which 1 to 5 carbon atoms can be replaced with heteroatoms such as N,O,S or $(C_5-C_{14})$-aryl-$(C_1-C_8)$alkyl, in which 1 to 5 carbon atoms in the aryl part can be replaced with heteroatoms such as N,O,S and $R_{11}$ has the same values as $R_{10}$ with the exception of hydrogen.

In the compounds of formula (I), the $R_1$ and $R_2$ radicals preferably represent a hydrogen atom or together form a saturated or unsaturated divalent alkylene radical containing 2 to 5 carbon atoms and in particular 2 to 4 carbon atoms and quite particularly 2 or 3 carbon atoms, which alkylene radical is non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$ alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, said divalent alkylene radical being able to be attached at the level of the carbon-carbon bond to a carbocycle or a heterocycle with 5 to 7 members, containing 1 or 2 nitrogen atoms, saturated or unsaturated, non-substituted or substituted by 1 or 2 $R_3$ radicals.

Among the compounds of formula (I), $R_1$ and $R_2$ preferably represent a hydrogen atom or a —$(CH_2)_p$— group, in which p is 2, 3, 4 or 5, preferably 2, 3 or 4, quite particularly 2 or 3, and which is non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$ alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, said —$(CH_2)_p$— radical being able to be attached at the level of the carbon-carbon bond to a carbocycle or a heterocycle with 5 to 7 members, containing 1 or 2 nitrogen atoms, saturated or unsaturated, non-substituted or substituted by 1 or 2 $R_3$ radicals.

$R_3$ is preferably an alkyl or alkoxy group containing 1 to 4 carbon atoms.

$R_4$ is preferably a hydrogen atom or an alkyl group containing 1 to 6 carbon atoms, non-substituted or substituted by a group chosen from $(C_1-C_4)$-alkoxy, $(C_1-C_4)$-alkyl-$S(O)_2$ and $NR_9R_9'$ in which $R_9$ and $R_9'$ independently from one another represent a hydrogen atom or $(C_1-C_4)$-alkyl. $R_4$ is quite particularly a hydrogen atom or an alkyl group containing 1 to 4 carbon atoms non-substituted or substituted by the radicals mentioned above.

$R_5$ is preferably a hydrogen atom, a $CO_2R_6$, $SO_2R_6$, $SO_2NHR_6$ or $SO_2NHCO_2R_6$ group $R_6$ is preferably a $(C_1-C_8)$-alkyl or naphthyl radical, non-substituted or substituted by $R_3$, a (mono-, bi- or tri-)-cycloalkyl radical containing 3 to 12 carbon atoms or $(C_3-C_{12})$ (mono-, bi- or tri-)-cycloalkyl-$(C_1-C_6)$-alkyl or the radical of formula (II)

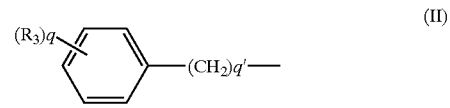

in which the $R_3$ radicals can be identical or different, and can be located in any position of the phenyl radical, q is equal to 0, 1, 2 or 3, preferably 0 or 1 and quite particularly 0 and q' is equal to 0 or 1. $R_6$ more particularly represents an alkyl radical containing 1 to 4 carbon atoms, a phenyl radical mono, bi or trisubstituted by $(C_1-C_6)$-alkyl, a naphthyl radical, an adamantylmethyl radical or the radical of formula (II) in which q is 0 or 1. $R_6$ quite particularly represents the radical of formula (II) with q equal to 0 or 1 and q' equal to 1, that is to say a benzyl radical non-substituted or monosubstituted in ortho, meta or para position by $R_3$.

$R_7$ is preferably a hydrogen atom or an alkyloxycarbonyl group containing 2 to 7 carbon atoms, more particularly hydrogen or alkyloxycarbonyl containing 2 to 5 carbon atoms and quite particularly hydrogen.

The preferred compounds of formula (I) are the compounds in which one or more radicals have the preferred meanings.

In particular, a subject of the invention is a compound of formula (I')

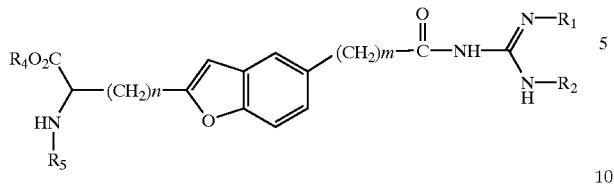

in which $R_1$ and $R_2$ represent a hydrogen atom or together form a saturated or unsaturated divalent alkylene radical containing 2 to 5 carbon atoms or more particularly represent a hydrogen atom or together form a —$(CH_2)_p$— group, in which p is 2, 3, 4 or 5, preferably 2, 3 or 4, quite particularly 2 or 3, said alkylene radical or —$(CH_2)_p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, said alkylene or —$(CH_2)_p$— group being able to be attached at the level of the carbon-carbon bond to a carbocycle or a heterocycle containing 1 or 2 atoms of nitrogen, with 5 to 7 members, saturated or unsaturated, non-substituted or substituted by $R_3$ and in particular by 1 or 2 $R_3$ radicals;

$R_3$ represents an alkyl or alkyloxy group containing 1 to 6 carbon atoms;

$R_4$ represents a hydrogen atom or an alkyl group containing 1 to 6 carbon atoms, non-substituted or substituted by a group chosen from $(C_1-C_4)$-alkoxy, $(C_1-C_4)$-alkyl-$S(O)_2$ and $NR_9R_9'$ in which $R_9$ and $R_9'$ independently from one another represent a hydrogen atom or $(C_1-C_4)$-alkyl;

$R_5$ represents a hydrogen atom, a $CO_2R_6$, $SO_2R_6$, $SO_2NHR_6$ or $SO_2NHCO_2R_6$ group in which $R_6$ is an alkyl radical containing 1 to 8 carbon atoms, a naphthyl radical, non-substituted or substituted by $(C_1-C_6)$-alkyl, a cycloalkyl radical containing 3 to 12 carbon atoms or $(C_3-C_{12})$-cycloalkyl-$(C_1-C_6)$alkyl or the radical of formula (II)

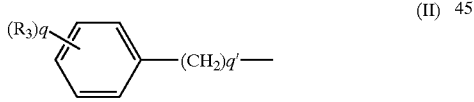

in which the $R_3$ radicals can be identical or different, and can be located in any position of the phenyl radical, q and q' are equal to 0 or 1;

m is an integer equal to 1, 2 or 3;

n is an integer equal to 1, 2 or 3;

said compounds of formula (I') being in all their possible isomer forms, alone or in a mixture in any ratio, as well as their physiologically acceptable salts and their pro-drugs.

A more particular subject of the invention is a compound of formula (I'), in which, $R_1$ and $R_2$ represent a hydrogen atom or together form a saturated or unsaturated divalent alkylene radical containing 2 to 4 carbon atoms or more particularly represent a hydrogen atom or together form a —$(CH_2)_p$— group, in which p is 2, 3 or 4, said alkylene radical or —$(CH_2)_p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$alkyl, $(C_5-C_{14})$-heteroaryl, $(C_5-C_{14})$-heteroaryl-$(C_1-C_6)$-alkyl, $(C_3-C_{12})$-cycloalkyl, $(C_3-C_{12})$-cycloalkyl-$(C_1-C_6)$-alkyl and oxo, said alkylene or —$(CH_2)_p$— group being able to be attached at the level of the carbon-carbon bond to a carbocycle or a heterocycle containing 1 or 2 nitrogen atoms, 5 to 7 members, saturated or unsaturated, non-substituted or substituted by $R_3$ and in particular by 1 or 2 $R_3$ radicals;

$R_3$ represents a alkyl or alkyloxy group containing 1 to 6 carbon atoms;

$R_4$ represents a hydrogen atom or an alkyl group containing 1 to 6 carbon atoms;

$R_5$ represents a hydrogen atom, a $CO_2R_6$, $SO_2R_6$, $SO_2NHR_6$ or $SO_2NHCO_2R_6$ group in which $R_6$ is a $(C_1-C_8)$-alkyl or naphthyl radical, non-substituted or substituted by $R_3$, a cycloalkyl radical containing 3 to 12 carbon atoms or $(C_3-C_{12})$-cycloalkyl-$(C_1-C_6)$-alkyl or the radical of formula (II)

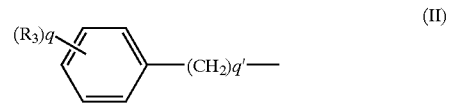

in which the $R_3$ radicals can be identical or different, and can be located in any position of the phenyl radical, q and q' are equal to 0 or 1;

m is an integer equal to 1, 2 or 3;

n is an integer equal to 1, 2 or 3;

said compounds of formula (I) being in all their possible isomer forms, alone or in a mixture in any ratio, as well as their physiologically acceptable salts and their pro-drugs.

A more particular subject of the invention is a compound of formula (I'), in which $R_1$ and $R_2$ represent a hydrogen atom or together form a saturated or unsaturated divalent alkylene radical containing 2 to 3 carbon atoms or more particularly represent a hydrogen atom or together form a —$(CH_2)_p$— group, in which p is 2 or 3, said alkylene radical or —$(CH_2)_p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$alkyl, $(C_5-C_{14})$-heteroaryl, $(C_5-C_{14})$-heteroaryl-$(C_1-C_6)$-alkyl, $(C_3-C_{12})$-cycloalkyl, $(C_3-C_{12})$-cycloalkyl-$(C_1-C_6)$-alkyl and oxo, said alkylene or —$(CH_2)_p$— group being able to be attached at the level of the carbon-carbon bond to a carbocycle or a heterocycle containing 1 or 2 atoms of nitrogen, with 5 to 7 members, saturated or unsaturated, non-substituted or substituted by $R_3$ and in particular by 1 or 2 $R_3$ radicals;

$R_3$ represents an alkyl or alkyloxy group containing 1 to 6 carbon atoms;

$R_4$ represents a hydrogen atom or an alkyl group containing 1 to 6 carbon atoms; $R_5$ represents a hydrogen atom, a $CO_2R_6$, $SO_2R_6$, $SO_2NHR_6$ or $SO_2NHCO_2R_6$ group in which $R_6$ is a $(C_1-C_8)$-alkyl or naphthyl radical, non-substituted or substituted by $R_3$, a cycloalkyl radical containing 3 to 12 carbon atoms or $(C_5-C_{15})$-cycloalkyl-$(C_1-C_6)$-alkyl or the radical of formula (II)

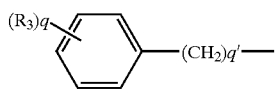

(II)

in which the $R_3$ radicals can be identical or different, and can be located in any position of the phenyl radical, q and q' are equal to 0 or 1;

m is an integer equal to 2;

n is an integer equal to 1;

said compounds of formula (I) being in all their possible isomer forms, alone or in a mixture in any ratio, as well as their physiologically acceptable salts and their prodrugs. Among the preferred compounds of formula (I), there are the compounds in which the asymmetrical carbon carrying the $CO_2R_4$ and $NHR_5$ groups is of S configuration.

A quite particular subject of the invention is the compounds of formula (I) or (I') as defined above in which $R_5$ is a $CO_2R_6$ radical, $R_6$ being as defined above and in particular $-CH_2Ph$, $-C(CH_3)_3$ and $CH_2$-Adamantyl, said compounds of formula (I) being in all their possible isomer forms, alone or in a mixture in any ratio, as well as their physiologically acceptable salts and their prodrugs.

A quite particular subject of the invention is the compounds of formula (I) or (I') as defined above in which $R_5$ is a $SO_2R_6$ radical, $R_6$ being as defined above and in particular alkyl containing 1 to 6 carbon atoms, naphthyl and phenyl substituted by one or more alkyl radicals containing 1 to 6 carbon atoms or $CF_3$ group, said compounds of formula (I) being in all their possible isomer forms, alone or in a mixture in any ratio, as well as their physiologically acceptable salts and their prodrugs.

A quite particular subject of the invention is the compounds of formula (I) or (I') as defined above in which $R_5$ is a $SO_2NHR_6$ or $SO_2NHCO_2R_6$ radical, $R_6$ being as defined above and in particular $-CH_2Ph$, $-C(CH_3)_3$ and $CH_2$-Adamantyl, said compounds of formula (I) being in all their possible isomer forms, alone or in a mixture in any ratio, as well as their physiologically acceptable salts and their prodrugs.

A subject of the invention is also the compounds of formula (I) the names of which follow:

5-[3-oxo-3-[(1,4,5,6-tetrahydro-2-pyrimidinyl)amino)-propyl]-.alpha.-[[(phenylmethoxy)carbonyl]amino]-2-benzofuranepropanoic acid, 1-methylethyl 5-[3-oxo-3-[(1,4,5,6-tetrahydro-2-pyrimidinyl)amino]propyl-.alpha.-[[(phenylmethoxy)carbonyl]amino]-2-benzofuranpropanoate, ethyl 5-[3-oxo-3-[(1,4,5,6-tetrahydro-2-pyrimidinyl)amino]-propyl]-.alpha.-[[(phenylmethoxy)carbonyl]amino]-2-benzofuranpropanoate, 5-[3-oxo-3-[(1,4,5,6-tetrahydro-2-pyrimidinyl)amino]-propyl]-.alpha.-[[[(tricyclo[3.3.1.1$^{3,7}$]dec-1-yl)methoxy]-carbonyl]amino]-2-benzofuranpropanoic acid, 5-[3-oxo-3-[(1,4,5,6-tetrahydro-2-pyrimidinyl)-amino] propyl]-.alpha.-[[[[(tricyclo[2,3,1,1$^{3,7}$]dec-1-yl) methoxy]carbonyl]amino]sulphonyl]amino]-2-benzofuranpropanoic acid, 5-[3-oxo-3-[(1,4,5,6-tetrahydro-2-pyrimidinyl)amino]-propyl]-.alpha.-[[[[(phenyl)methoxy]carbonyl]-amino]-sulphonyl]amino]-2-benzofuranpropanoic acid, .alpha.-[[[(phenylmethyl)-amino]sulphonyl]amino]-5-[3-oxo-3-[(1,4,5,6-tetrahydro-2-pyrimidinyl)amino]propyl]-2-benzofuranpropanoic acid, .alpha.-[[[4-(1,1-dimethylethyl)phenyl]-sulphonyl]-amino]-5-(3-oxo-3-[(1,4,5,6-tetrahydro-2-pyrimidinyl)amino]-propyl]-2-benzofuranpropanoic acid, .alpha.-[[[4-(1-methylethyl)phenyl]sulphonyl]amino]-5-(3-oxo-3-[(1,4,5,6-tetrahydro-2-pyrimidinyl)amino]propyl]-2-benzofuranpropanoic acid, 5-[3-oxo-3-[(1,4,5,6-tetrahydro-2-pyrimidinyl)-amino] propyl]-.alpha.-[propylsulphonyl)amino]-2-benzofuranpropanoic acid, .alpha.-[methylsulphonyl)amino]-5-[3-oxo-3-[(1,4,5,6-tetrahydro-2-pyrimidinyl)amino]propyl]-2-benzofuranpropanoic acid, .alpha.-[(1-naphthalenylsulphonyl)amino]-5-[3-oxo-3-[(1,4,5,6-tetrahydro-2-pyrimidinyl)amino]propyl]-2-benzofuranpropanoic acid, 1-methylethyl alpha.-[(1-naphthalenylsulphonyl)amino]-5-[3-oxo-3-[(1,4,5,6-tetrahydro-2-pyrimidinyl)amino] propyl]-2-benzofuranpropanoate, as well as their physiologically acceptable salts and their prodrugs.

A subject of the present invention is also a process for the preparation of the compounds of formula (I). The compounds can generally be prepared, for example during convergent synthesis by coupling two or several fragments which can be derived by retrosynthesis of the compounds of formula (I). In order to avoid the functional groups from leading to undesirable or secondary reactions during each stage of synthesis, it can be advantageous or necessary during the synthesis of the compounds of formula (I), to introduce the functional groups in the form of precursors which are then converted into the desired functional groups or to temporarily block these functional groups by implementing a protective group strategy appropriate for the synthesis which is known to a person skilled in the art (Greene, Wuts Protective Group in Organic Synthesis, Wiley 1991).

Thus the compounds of formula (I) can be prepared, for example, by implementing the following stages a) formation of a carboxylic acid or a derivative of carboxylic acid of formula (III)

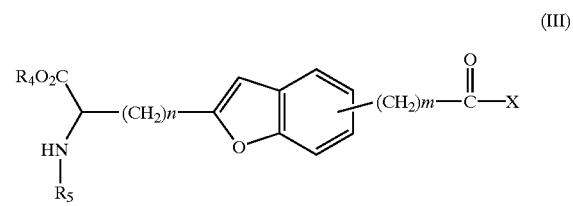

(III)

in which $R_4$, $R_5$, n and m are as defined above for formula (I) and in which X is a parting group which can be substituted by a nucleophile, by the action of the aminoester of formula (V)

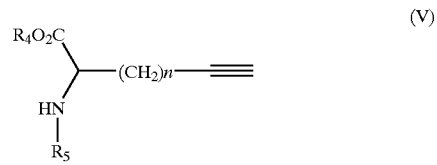

(V)

in which $R_4$, $R_5$, and n are as defined above for formula (I), with a carboxylic acid or a derivative of carboxylic acid of formula (VI), in the presence of a catalyst and in a basic medium

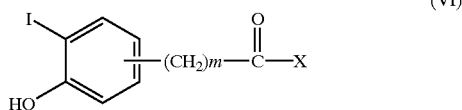

in which m and X are as defined above, the functional groups, optionally present in the form of precursors or in protected form, then being converted to groups present in the compounds of formula (I) and b) coupling the carboxylic acid or the carboxylic acid derivative of formula (III) as defined above with a guanidine or a guanidine derivative of formula (IV)

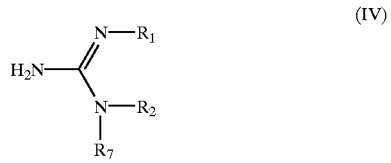

in which $R_1$, $R_2$ and $R_7$ are as defined in formula (I), the functional groups optionally present in the form of precursors or in protected form then being converted to groups present in the compounds of formula (I).

The formation of a carboxylic acid or of a carboxylic acid derivative of formula (III) by the action of the amino ester of formula (V) with carboxylic acid or a carboxylic acid derivative of formula (VI) is preferably carried out in the presence of a copper oxide such as $Cu_2O$ in a solvent such as pyridine.

The COX group in formula (III) or (VI) is preferably the carboxylic acid group or an activated derivative of carboxylic acid. X for example is hydroxyl or halogen, in particular chlorine or bromine, alkoxy, preferably methoxy or ethoxy, aryloxy, for example phenoxy or pentafluorophenoxy, phenylthio, methylthio, 2-pyridylthio or a nitrogenous heterocycle linked via a hydrogen atom, in particular an azole such as for example 1-imidazolyl. X can also be for example (($C_1$–$C_4$)-alkyl)-O—CO—O— or tolylsulphonyloxy and the activated acid derivative can be a mixed anhydride.

If X is a hydroxyl, therefore if the guanidine of formula (IV) reacts with a carboxylic acid of formula (III), then the carboxylic acid is first activated. Activation can be carried out for example using dicyclohexylcarbodiimide (DCCI) or with the O—((cyano(ethoxycarbonyl)-methylene)amino)-1, 1,3,3-tetramethyluronium tetrafluoroborate (TOTU; König et al, Proc. 21st Europ. Peptide Symp. 1990 (Eds Giralt, Andreu), Escom, Leiden 1991, p.243) or another activation agent currently used in petptide synthesis.

Apart from the free guanidines of formula (IV), the guanidine salts can also be used in the reaction with the compounds of formula (III), the free guanidines being formed in situ or by a separate stage by means of a base.

The reaction of an activated carboxylic acid derivative of formula (III) with the guanidine (or derivative) of formula (IV) is preferably carried in a manner known per se in an organic protic or aprotic but inert solvent. In this case, solvents are used such as methanol, isopropanol, tert-butanol, dimethylformamide or tetrahydrofuran at temperatures ranging from 0° C. to the reflux temperature of these solvents, in particular during the reaction of the methyl or ethyl esters (X is a methoxy or an ethoxy) with guanidines.

The reactions of the COX type compounds with the free guanidines are advantageously carried out in an inert aprotic solvent such as dimethylformamide, tetrahydrofuran, dimethoxyethane or dioxane, if appropriate by adding a base such as for example potassium tert-butoxide or sodium methoxide. However, water can also be used as a solvent in the reactions of the compounds of formula (III) with the guanidines of formula (IV), for example by using a base such as sodium hydroxide.

If X is chlorine, the reaction will preferably be carried out by adding an acid trap, for example a base or an excess of guanidine (or derivative). The reaction mixture is then treated and if desired, the reaction product is purified according to methods known to a person skilled in the art.

The protective groups optionally present in the compounds obtained from the compounds of formulae (V), (VI), (III) and (IV) are then eliminated by standard processes, for example the tert-butyl ester groups are converted to carboxylic acid by treatment with trifluoroacetic acid, the benzyl groups are eliminated by hydrogenation or also the fluorenylmethoxy-carbonyl groups are eliminated in the presence of secondary amine and other reactions are carried out using standard processes, for example by acylation reactions. If necessary, the conversion into physiologically acceptable salts is carried out by processes known to a person skilled in the art.

When $R_5$ represents a hydrogen atom, the functionalization of the amine to a group present in the compounds of formula (I), i.e. in particular when $R_5$ represents a $CO_2R_6$, $SO_2R_6$, $SO_2NHR_6$ or $SO_2NHCO_2R_6$ group is carried out at the level of the compounds of formula (V), (III) or (I) and preferably (III). For example in order to obtain the compounds of formula (III) with $R_5$=$CO_2R_6$ from the corresponding amine, a compound of formula X'—$CO_2R_6$, X' being a parting group and in particular O-succinic or also a halogen is reacted. In order to obtain the compounds of formula (III) with $R_5$=$SO_2R_6$ from the corresponding amine a compound of formula $R_6SO_2X'$ is reacted, X' being in particular a halogen.

In order to obtain the compounds of formula (III) with $R_5$=$SO_2NHCO_2R_6$ from the corresponding amine a compound of formula X'$SO_2NHCO_2R_6$ is reacted, X' being in particular a halogen or preferably by the action of an isocyanate of formula $ClSO_2NCO$ in the presence of an $R_6OH$ alcohol. Finally, in order to obtain the compounds of formula (III) with $R_5$=$SO_2NHR_6$ from the corresponding amine an isocyanate of $ClSO_2NCO$ type is firstly reacted in the presence of a terbutyl alcohol, then a halide of formula $R_6X$ and finally a deprotection agent of the BOC group.

The compounds of formula (IV) are commercially available or easily accessible to a person skilled in the art. The compounds of formula (VI) are also known or also easily accessible to a person skilled in the art, in particular according to the methods described below in Preparation 3.

The compounds of formula (V) can be prepared according to processes described in the International Application WO97/40052 or also are accessible by analogy. This process is illustrated in the diagram described below, it being understood that the present invention is not restricted to these syntheses or these starting products. It is not a major difficulty for a person skilled in the art to envisage modifications to syntheses described in our Application for the preparation of other compounds of formula (I) according to the invention.

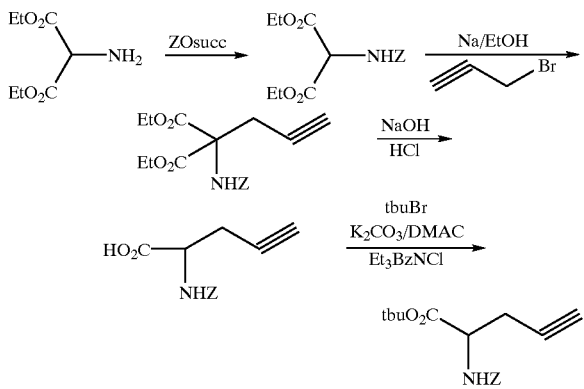

The compounds of formula (I) are compounds having a pharmacological activity and can thus be used as medicaments in the treatment or prevention of bone diseases, tumorous diseases as well as cardiovascular disorders.

The compounds of formula (I) as well as their physiologically acceptable salts and their prodrugs can be administered to animals, preferably mammals and in particular human beings as therapeutic or prophylactic medicaments. They can be administered as they are or in a mixture with one or more other compounds of formula (I) or also in the form of a pharmaceutical preparation (pharmaceutical composition) which allows enteral or parenteral administration and which contains an effective dose of at least one compound of formula (I) and/or its physiologically acceptable salts and/or its prodrugs as active ingredient as well as current and pharmaceutically inert supports and/or additives.

A subject of the present invention is therefore the compounds of formula (I) and/or their physiologically acceptable salts and/or their prodrugs as medicaments.

A subject of the present invention is also the use of the compounds of formula (I) and/or their physiologically acceptable salts and/or their prodrugs for the preparation of medicaments intended for the prevention or treatment of the diseases mentioned above or below, for example for the treatment or prevention of bone diseases.

A subject of the present invention is also pharmaceutical compositions which allow enteral or parenteral administration and which contain an effective dose of at least one compound of formula (I) and/or its physiologically acceptable salts and/or its prodrugs as active ingredient such as one or more usual pharmaceutically inert supports and if appropriate one or more additives.

The medicaments can be administered orally, for example in the form of pills, tablets, coated tablets, film-encased, granules, gelatin capsules and soft capsules, solutions, syrups, emulsion, suspension or aerosol mixtures. The administration can however be carried out by rectal route, for example in the form of suppositories or by parenteral route, for example in the form of injectable solutions, infusions, microcapsules or implants or by percutaneous route, for example in the form of an ointment, solutions, pigments or colorants or by of other routes such as in the form of an aerosol or nasal spray.

The pharmaceutical preparations according to the invention are prepared according to methods known per se, pharmaceutically inert organic or inorganic supports, being added to the compounds of formula (I) and/or their physiologically acceptable salts and/or their prodrugs. For the production of pills, tablets, coated tablets and hard gelatin capsules, it is possible to use for example lactose, corn starch or its derivatives, talc, stearic acid or its salts, etc. Suitable supports for soft gelatin capsules or for suppositories are for example fats, waxes, semi-solid or liquid polyols, natural or modified oils, etc. Appropriate vehicles for the preparation of solutions, for example injectable solutions, emulsions or syrups are for example water, alcohols, glycerol, polyols, sucrose, inverted sugars, glucose, vegetable oils, etc.

Suitable supports for microcapsules or implants are for example glyoxilic acid and lactic acid copolymers. The pharmaceutical preparations normally contain from 0.5% to 90% by weight of the compounds of formula (I) and/or their physiologically acceptable salts.

In addition to the active ingredients and supports, the pharmaceutical preparations can contain additives such as, for example, diluting agents, disintegration agents, binding agents, lubricants, wetting agents, stabilisers, emulsifiers, preservatives, sweetening agents, colouring agents, flavouring or aromatizing agents, thickeners, buffering agents, and also solvents or solubilizing agents or agents to obtain a delayed release effect and also salts for modifying the osmotic pressure, coating agents or antioxidants. They can also contain two or more compounds of formula (I) and/or their physiologically acceptable salts and/or their prodrugs. Moreover, in addition to at least one or more compounds of formula (I) and/or their physiologically acceptable salts and/or their prodrugs, they can contain at least one or more active ingredients which can be used for therapeutic or prophylactic uses.

The pharmaceutical compositions normally contain 0.2 to 500 mg, and preferably 1 to 200 mg of the compound of formula (I) and/or their physiologically acceptable salts and/or their prodrugs.

The compounds of formula (I) are quite particularly antagonists of the vitronectin receptors and are therefore capable for example of inhibiting the adhesion of osteoclasts on the surface of the bone and thus bone resorption by the osteoclasts.

The action of the compounds of formula (I) can be demontstrated for example in a test in which the inhibition of the binding of vitronectin to the cells which contain the vitronectin receptor is determined. Further information about this test is given below.

As antagonists of the vitronectin receptor, the compounds of formula (I) and their physiologically acceptable salts and their prodrugs are in general suitable for the treatment or prevention of diseases linked to the interactions between the vitronectin receptors and their ligands, in the process of cell-cell or cell-matrix interaction or which can be influenced by the inhibition of interactions of this type, to relieve or cure when inhibition of interactions of this type is desired.

As explained at the beginning, such an interaction plays an important role in bone resorption, in angiogenesis or in cell proliferation of the smooth muscle vascular cells. Bone diseases in which the treatment or prevention require the use of the compounds of formula (I) are in particular osteoporosis, hypercalcemia, osteopenia, for example caused by bony metastases, dental disorders for example parodontitis, hyperparathyroidism, periarticular erosions in rheumatoid arthritis, and Paget's disease. Moreover the compounds of formula (I) can be used to relieve, prevent or treat bone disorders which are caused by treatments with glucocorticoids, therapies linked to taking steroids or corticosteroids or male or female sex hormone deficiences. All these disorders are characterized by bone loss, which is caused by a lack of equilibrium between bone formation and bone destruction and which can be favourably influenced by the inhibition of bone resorption by the osteoclasts. Besides this use as an inhibitor of bone resorption is mediated via the osteoclasts, the compounds of formula (I) and their physiologically acceptable salts and their prodrugs are used as inhibitors of tumourous growth or of cancerous metastases, in the treatment of inflammatory disorders, for the treatment or prevention of cardiovascular disorders, such as arteriosclerosis or the recurrence of stenosis, or the treatment or prevention of nephropathy or retinopathy such as for example diabetic retinopathy.

The compounds according to the invention can also have an activity with respect to other integrins which interact with their ligands via the tripeptide sequence RGD ($\alpha_v\beta_1$, $\alpha_v\beta_5$, $\alpha_{IIb}\beta_3$), giving them pharmacological properties which can be used to treat pathologies associated with these receptors. This activity vis a vis the integrins therefore makes the compounds of formula (I) of use in the prevention or treatment of numerous diseases such as those mentioned above or in the publication by Dermot Cox DN§P 8(4) May 1995, 197–205 the content of which is incorporated in the present Application.

When the compounds of formula (I) are used, the doses can vary within wide limits and must be set according to the person treated. This depends for example on the compound used and the nature and severity of the disease to be treated, whether the conditions are serious or acute and if a prophylactic treatment is used.

In the case of administration by oral route, the daily dose in general varies from 0.01 to 100 mg/kg and preferably from 0.1 to 50 mg/kg, in particular from 0.1 to 5 mg/kg. For example, for an adult weighing 75 kg, a daily dose can be envisaged varying from 0.3 to 0.5 mg/kg.

In the case of administration by intravenous route, the daily dose varies approximately from 0.01 to 100 mg/kg and preferably from 0.05 to 10 mg/kg.

The daily dose can be divided, in particular in the case of the administration of a large quantity of active ingredient, in several, for example 2, 3 or 4 parts. If appropriate, depending on individual behaviour, it may be necessary to administer different increasing or decreasing doses.

Apart from the use of the compounds of formula (I) as medicaments, it is also possible to envisage their use as a vehicle or support for active ingredients in order to deliver these active compounds specifically towards the target (Drug targeting, see Targeted Drug Delivery, R. C. Juliano, Handbook of Experimental Pharmacology, Vol 100, Ed. Born, G. V. R. et al, Springer Verlag). The active ingredients which can be delivered are in particular those used for the treatment or prevention of the diseases quoted above.

The compounds of formula (I) and their salts can also be used as a diagnostic agent, for example for in vitro methods or as auxiliaries in biochemical studies in which blocking the vitronectin receptor or influencing cell-cell or cell-matrix interactions are desired. They can moreover be used as an intermediate for the preparation of other compounds, in particular other active ingredients, which are accessible from the compounds of formula (I), for example by modification or introduction of radicals or functional groups.

EXAMPLES

The products were identified by mass spectrometry (MS), infrared (IR) and/or NMR spectrometry. The compounds, which were purified by chromatography using a eluent which contains for example acetic or trifluoroacetic acid, and which are then dried or in which during the last stage of synthesis, trifluoroacetic acid for example was used to eliminate a tert-butyl protective group, sometimes containing, depending on the manner in which the product was dried, the acid originating from the eluent or from the last stage of synthesis and therefore is partially or completely in the form of the salt of the acid used, for example in the form of a salt of acetic or trifluoroacetic acid. They can also be more or less hydrated.

Abbreviations/chemical Names Optionally Used

PCC: pyridine chlorochromate DMF; DMF: dimethylformamide;
THF: tetrahydrofuran; MeOH: methanol; AcOEt: ethyl acetate;
TFA: trifluoroacetic acid; TEA: triethylamine; BTEAC: benzyltriethylammonium chloride; DMAC: dimethylacetamide; sh. (Shoulder); S (strong); s (singlet); d (doublet); t (triplet); b (broad); m (multiplet).

PREPARATION 1 (P1)

1,1-dimethylethyl 5-(3-methoxy-3-oxopropyl)-.alpha.[[(phenylmethoxy)carbonyl]-amino]-2-benzofuranepropanoate

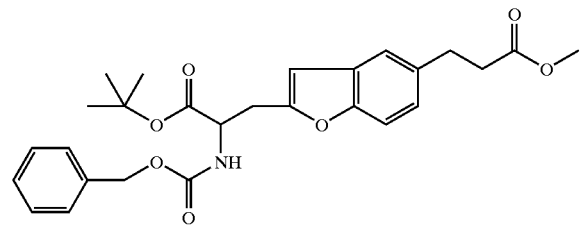

Stage a: Alkylation diethyl 2-[[(phenylmethoxy)carbonyl]amino]-2-propynylpropanedioate A solution of sodium ethylate previously prepared from 500 mg of sodium in 20 ml of ethanol is added to 6 g of diethyl 2-[[(phenylmethoxy)carbonyl]amino]-propanedioate (prepared according to Bladon. C. M. J. Chem. Soc. Perkin. Trans I 9, 1151–1158 (1990) in 30 ml of ethanol then, after 30 minutes, 3 g of propargyl bromide at 80% in toluene is added and the reaction mixture is heated under reflux for 1 hour. The reaction mixture is then brought back to ambient temperature followed by evaporation under reduced pressure, taking up in dichloromethane, washing and drying. After evaporation under reduced pressure 6 g of the expected product is obtained which is purified by chromatography, eluting with a Cyclohexane/Ethyl acetate mixture 85/15. 2.82 g of purified product is obtained.

Stage b: Saponification+Decarboxylation

2-[[(phenylmethoxy)carbonyl]amino]-4-pentynoic acid 6.75 ml of soda is added to 4.5 g of the product obtained in the previous stage in 45 ml of methanol and the reaction medium is agitated for 4 hours, then the pH is adjusted to 4.2–4.3 by the addition of 2N hydrochloric acid, followed by extracting with ethyl acetate, washing, drying and evaporating under reduced pressure until 4.7 g of crude product (intermediate diacid) is obtained. Then 40 ml of dioxane is added, the reaction medium is taken to reflux for 1 hour, then evaporated under reduced pressure until 3.51 g of expected decarboxylated product is obtained.

MS: 246-=[M–H]⁻; 138⁻=[M–OCH₂Ph]⁻

Stage c: Esterification 1,1-dimethylethyl 2-[[(phenylmethoxy)carbonyl]amino]-4-pentynoate.

25.75 g of potassium carbonate, 1.66 g of triethylbenzylammonium hydrochloride (BTEAC) and 30 ml of ter-butyl bromide are added to 2.6 g of the acid obtained in the previous stage in 65 ml of DMAC, and agitation is carried out for 16 hours and 45 minutes at 60° C. After cooling to ambient temperature, the reaction medium is filtered, washed, dried and evaporated under reduced pressure. 2.75 g of expected product is obtained.

IR (CHCl$_3$) NH 3429 cm$^{-1}$; C≡CH 3309 cm$^{-1}$; C=O 1719 cm$^{-1}$; Amide II and Ph-CH$_2$— 1508 cm$^{-1}$.

Stage d: Formation of the benzofurane 1,1-dimethylethyl 5-(3-methoxy-3-oxopropyl)-.alpha.[[(phenylmethoxy)carbonyl]-amino]-2-benzofuranepropanoate 2.3 g of the iodated P3 derivative, 800 mg of Cu$_2$O, 25 ml of pyridine are added to 2.38 g of the ester prepared in the previous stage then brought to reflux for 14 hours. After returning to ambient temperature, the reaction medium is filtered, rinced with ethyl acetate, evaporated under reduced pressure and the residual pyridine is eliminated by co-distilling with toluene. The reaction medium is purified by chromatography eluting with a dichloromethane/ethyl acetate mixture 95/5 then 97/3 and the product is taken up in ethyl acetate, washed, dried and evaporated under reduced pressure until 3.3 g of expected product is obtained which is repurified by chromatography eluting with a cyclohexane/ethyl acetate mixture 8/2. 2.86 g of pure expected product is obtained.

NMR (CDCl$_3$) 1.44 (s, Boc); 2.65(t, 2H); 3.01 (t, 2H) 3.29 (bd, 2H); 4.60 (m, 1H); 5.43 (d, 1H); 3.67 (s, 3H); 5.10 (AB, 2H) 6.39 (s, 1H); 7.05 (dd, 1H); 7.25 to 7.40 (m, aromatic 7H)

Preparation 2 (P2): Deprotection of P1

1,1-dimethylethyl.alpha.amino-5-(3-methoxy-3-oxopropyl)-2-benzofuranepropanoate

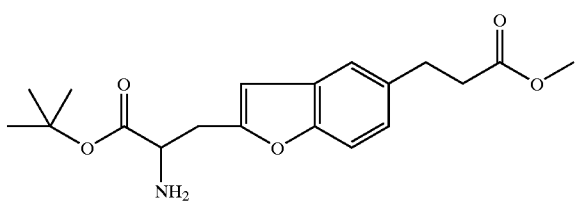

700 mg of palladium on carbon is added to 1.05 g of the protected amine of preparation 1 in 50 ml of methanol, the argon is purged and a currant of hydrogen is passed through, then after filtration, the solution is evaporated under reduced pressure until 626 mg of expected deprotected product is obtained.

Preparation 3 (P3)

methyl 4-hydroxy-3-iodobenzenepropanoate

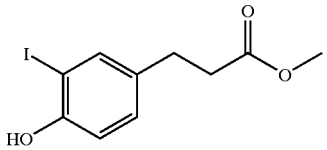

This compound is prepared according to the methods described by F. G. Schreiber et al. (Chem. Lett. (1975) 1257–1258; J. Chem. Soc. Perkin Trans (1976) 1514–1518), by B. Loev et al. (Tet. Lett (1974) 13, 1101–1103) or also by electrophilic iodation of the corresponding non-iodated methyl 4-hydroxybenzene-propanoate derivative by the action of iodine in the presence of sodium hypochlorite then of soda in methanol.

Example 1

5-[3-oxo-3-[(1,4,5,6-tetrahydro-2-pyrimidinyl)amino)propyl]-.alpha.-[[(phenylmethoxy)carbonyl]-amino]-2-benzofuranepropanoic acid

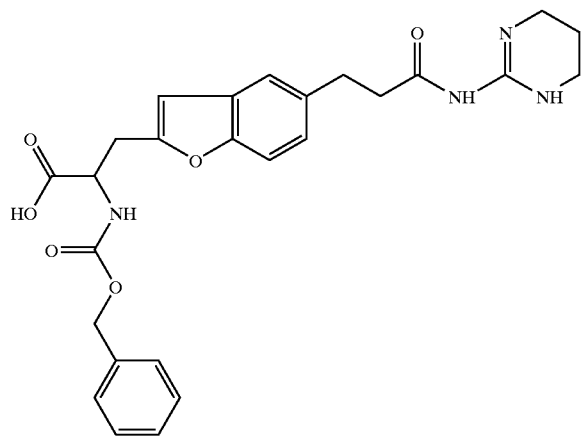

Stage a: Formation of the acylguanidine 1,1-dimethylethyl 5-[3-oxo-3-[(1,4,5,6-tetrahydro-2-pyrimidinyl)amino)propyl]-.alpha.-[[(phenylmethoxy)carbonyl]amino]-2-benzofuranepropanoate 620 mg of cyclic guanidine (1,4,5,6-tetrahydro-2-pyrimidinamine) is added to 1.5 g of product obtained in Preparation 1 (P1) in 10 ml of THF and agitation is carried out for 4 hours 30 minutes under nitrogen at ambient temperature. After evaporation under reduced pressure, 4.2 g of crude product (2 experiments were combined) is purified by chromatography eluting with a solvent A/ethyl acetate mixture 1/1 (solvent A: CHCl$_3$ 70, MeOH 30, AcOH 6, H$_2$O 3). 1.1 g of expected product is obtained Rf=0.25 (solvent A/Ethyl acetate 1/1).

Stage b: Hydrolysis of the ester

5-[3-oxo-3-[(1,4,5,6-tetrahydro-2-pyrimidinyl)amino)-propyl]-.alpha.-[[(phenylmethoxy)carbonyl]amino]-2-benzo-furanepropanoic acid.

12 ml of trifluoroacetic anhydride is added to 1.09 g of the ester obtained in the previous stage in 12 ml of dichloromethane, the reaction medium is agitated for 3 hours at ambient temperature and evaporated under reduced pressure until 1.06 g of expected product is obtained which is purified by chromatography eluting with a Solvent A/Ethyl acetate 1.5/0.5 mixture, in order to obtain 893 mg of amorphous product which is taken up in 10 ml of CH$_2$Cl$_2$ and 10 ml of TFA. 953 mg of pure expected product is obtained after evaporation under reduced pressure.

NMR (CDCl$_3$) 1.91 (m, CH$_2$ in position 5'); 2.80 (bt) 3.02 (m) =C—CH$_2$—CH$_2$—Ar; 3.37 (m, 6H CH$_2$ in position 4' and 6' and =C—CH$_2$—CH—NHCO); 4.75 (m,=C—CH$_2$—CH—NHCO); 5.13 (bs, —CO$_2$CH$_2$Ph); 5.60 (d, =C—CH$_2$—CH—NHCO); 7.01 (bd) 7.17 (bd) 7.24 (masked) phenyl of the benzofurane; 7.35 (bs, phenyl of the benzyl); 9.95 (bs, mobile H's)

SM 493$^+$=MH$^+$; 985$^+$=2MH$^+$

Example 2

1-methylethyl 5-[3-oxo-3-[(1,4,5,6-tetrahydro-2-pyrimidinyl)amino]propyl-.alpha.-[[(phenylmethoxy)carbonyl]amino]-2-benzofuranpropanoate

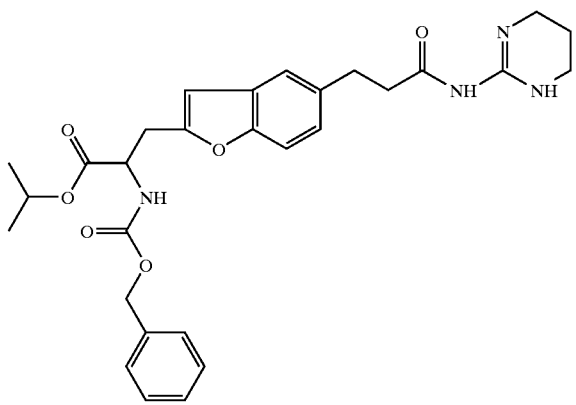

25 ml of isopropanol and 100 mg of sulphuric acid are added to 700 mg of the terbutyl ester of Example 1, and the reaction medium is taken to reflux for 14 hours then another 100 mg of sulphuric acid is again added and reflux continued for 24 hours. After evaporation under reduced pressure, the reaction medium is taken up in ethyl acetate, followed by washing, drying, evaporating under reduced pressure, purifying by chromatography eluting with a solvent A/Ethyl acetate 1/1 mixture, and 493 mg of product is obtained which is taken up in THF and 2 ml of hydrochloric acid. The reaction medium is evaporated under reduced pressure while adding toluene and recrystallized from ether. 476 mg of pure product is obtained.

NMR (CDCl$_3$)

1.24 (m, (CH$_3$)$_2$CHOCO—); 5.06 (m, (CH$_3$)$_2$CHOCO—); 2.02 (m, CH$_2$ in 5'); 2.90 (bt) 3.02 (m) =C—CH$_2$—CH$_2$—Ar; 3.46 (m, CH$_2$ in position 4' 6'); 3.31 (d, =C—CH$_2$—CH—NHCO); 4.68 (m, =C—CH$_2$—CH—NHCO); 5.49 (d, =C—CH$_2$—CH—NHCO); 5.10 (AB, —CO$_2$CH$_2$Ph); 6.40 (s, H3); 7.08 to 7.40 (m, aromatic H); 9.41 (s, 2H) 12.81 (s, 1H) mobile H's.

Example 3 ethyl 5-[3-oxo-3-[(1,4,5,6-tetrahydro-2-pyrimidinyl)amino]propyl]-.alpha.-[[(phenylmethoxy)carbonyl]amino]-2-benzofuranpropanoate

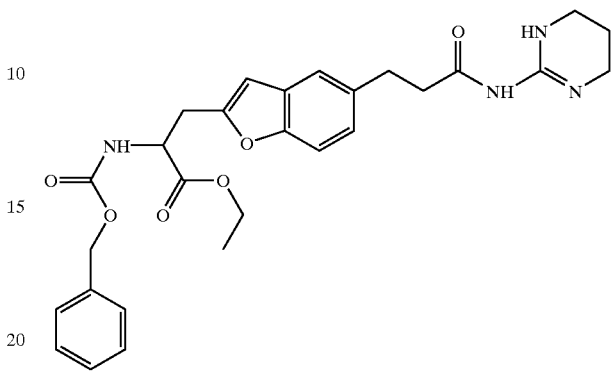

The operation is carried out as in Example 2 but in the presence of 10 ml of ethanol instead of isopropanol. 392 mg of expected product is obtained.

NMR (CDCl$_3$) 1.23 (m, CH$_3$CH$_2$OCO—); 4.13 (q) 4.23 (m) CH$_3$CH$_2$OCO—; 1.93 (m, CH2 in position 5'); 2.64 (m) 3.00 (m) =C—CH$_2$—CH$_2$-Ph; 4.48 (q) 4.71 CO—CH—NHCO; 5.10(m CH$_2$O); 5.51 (bs) 5.73 (d) 5.86 (d) NH—; 6.38 (s, H3); 7.09 (dd, H6); 7.24 to 7.35 (aromatic H's, H4, H7); 7.85 mobile H.

MS 521$^+$=[M+H]$^+$; 1041$^+$=[2M+H]$^+$; 519$^-$=[M–H]$^-$; 411$^-$=MH$^-$—OCH$_2$Ph.

Example 4

Monohydrochloride ethyl 5-[3-oxo-3-[(1,4,5,6-tetrahydro-2-pyrimidinyl)amino]propyl]-.alpha.-[[(phenylmethoxy)carbonyl]-amino]-2-benzofuranpropanoate

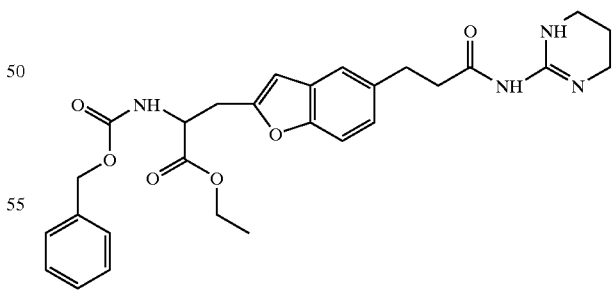

3 ml of 2N hydrochloric acid is added to 339 mg of the ethyl ester of Example 3 in 20 ml of THF, the reaction medium is agitated for 10 minutes and evaporated under reduced pressure while adding toluene. After treatment with ether and isopropyl ether, 312 mg of the expected hydrochloric acid salt is obtained.

Example 5

Mono(trifluoroacetate) of

5-[3-oxo-3-[(1,4,5,6-tetrahydro-2-pyrimidinyl)
amino]propyl]-.alpha.-[[[(tricyclo[3.3.1.1$^{3,7}$]dec-1-
yl)methoxy]carbonyl]amino]-2-benzofuranpropanoic
acid

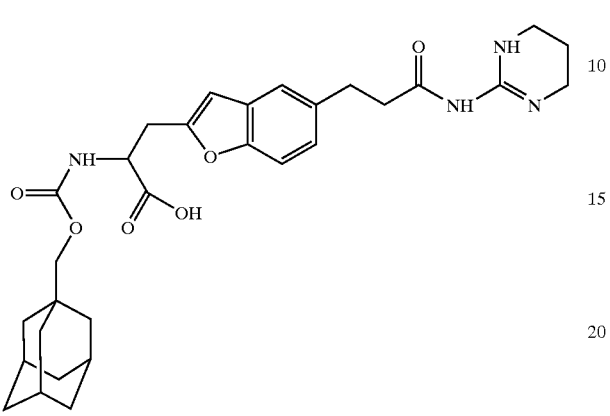

Stage a 1,1-dimethylethyl.alpha.-[[[(tricyclo[3.3.1.1$^{3,7}$]dec-
1-yl)methoxy]carbonyl]-amino]-5-(3-methoxy-3-
oxopropyl)-2-benzofuranpropanoate 78 μl of triethyamine and 164 mg of 1-[[[(tricyclo [3.3.1.1$^{3,7}$]dec-1-yl)methoxy]carbonyl]oxy]-2,5-pyrrolidinedione (cf J. Chem. Soc. Chem. Comm. (1992) 1308) is added under argon and at 0° C. to 150 mg of P2 amine in 10 ml of dichloromethane, and agitation is carried out for 18 hours while allowing the temperature to rise to ambient temperature. After washing and drying, the reaction medium is evaporated under reduced pressure until 288 mg of expected product is obtained.

IR (CHCl$_3$) NH 3434 cm$^{-1}$, C=O 1743 cm$^{-1}$ (Max), Conjuguated system+amide II: 1600, 1507 cm$^{-1}$.

Stage b: Amidification 1,1-dimethylethyl 5-[3-oxo-3-[(1,4,5,6-tetrahydro-2-
pyrimidinyl)amino]propyl]-.alpha.-[[[(tricyclo
[3.3.1.1$^{3,7}$]dec-1-yl)methoxy]carbonyl]-amino]-2-
benzofuranpropanoate The operation is carried out as in Example 1 starting from 220 mg of the ester prepared in Stage a and 80 mg of 1,4,5,6-tetrahydro-2-pyrimidinamine. 120 mg of expected product is obtained.

IR (CHCl$_3$) NH 3433; 3265 cm$^{-1}$, complex C=O 1712 cm$^{-1}$ (Max; C=O C=N 1658 cm$^{-1}$; Aromatic+C=C+ Amide II: 1601, 1574, 1508 cm$^{-1}$.

Stage c: hydrolysis of the terbutyl ester Mono (trifluoroacetate) of

5-[3-oxo-3-[(1,4,5,6-tetrahydro-2-pyrimidinyl)
amino]propyl]-.alpha.-[[[(tricyclo-[3.3.1.1$^{3,7}$]dec-1-
yl)methoxy]carbonyl]amino]-2-benzofuranpropanoic
acid 2 ml of trifluoroacetic acid is added to a solution of 120 mg of ester prepared in the previous stage in 1 ml of dichloromethane and agitation is carried out for 4 hours at ambient temperature. The reaction medium is evaporated under reduced pressure, taken up in a water/acetic acid mixture and lyophilised in order to obtain 65 mg of expected product MS: 551 Da=MH$^+$

Example 6

5-[3-oxo-3-[(1,4,5,6-tetrahydro-2-pyrimidinyl)
amino]-propyl]-.alpha.-[[[[(tricyclo[2.3.1.1$^{3,7}$]dec-
1-yl)methoxy]-carbonyl]amino]sulphonyl]amino]-2-
benzofuranpropanoic acid

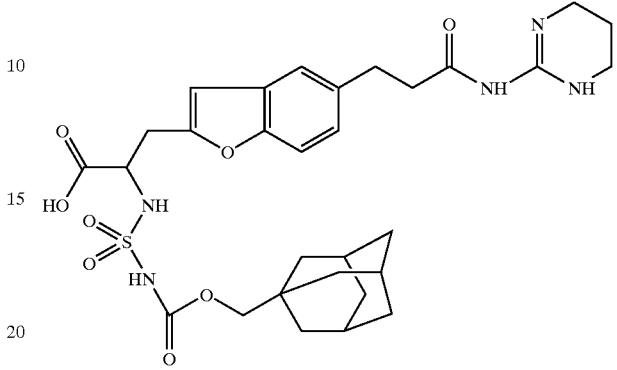

Stage a: Addition of chlorosulphonyl 1,1-dimethylethyl 5-(3-methoxy-3-oxopropyl)
.alpha.-[[[[[(tricyclo[2.3.1.1$^{3,7}$]-dec-1-yl)methoxy]
carbonyl]amino]sulphonyl]amino]-2-
benzofuranpropanoate 292 mg of tricyclo-[3.3.1.13,7]decane-1-methanol in 5 ml of dichloromethane is added to a solution of 250 mg of chlorosulphonyl isocyanate in 5 ml of dichloromethane and the reaction medium is agitated at 0° C. for 1 hour thirty minutes. Then 692 mg of P2 amine then 490 μl of TEA is added. After washing with a solution of 1N hydrochloric acid/NaHCO$_3$ then drying, the reaction medium is evaporated under reduced pressure and purified by filtration while washing with dichloromethane. After purification 0.88 g of expected product is obtained.

IR (CHCl$_3$) NH 3391 cm$^{-1}$; C=O 1736 cm$^{-1}$; conjuguated system+aromatic 1600, 1473 cm$^{-1}$.

Stage b: Amidification 1,1-dimethylethyl (3.alpha.,5.beta.,7.alpha.)-5-[3-
oxo-3-[(1,4,5,6-tetrahydro-2-pyrimidinyl)amino]
propyl]-.alpha.-[[[[[(tricyclo-[2.3.1.1$^{3,7}$]dec-1-yl)
methoxy]carbonyl]amino]sulphonyl]amino]-2-
benzofuranpropanoate The operation is carried out as in Example 1 but starting from 0.88 g of the ester prepared in the previous stage and 280 mg of (1,4,5,6-tetrahydro-2-pyrimidinamine). 220 mg of expected product is obtained.

NMR (CDCl$_3$) 1.43 (s, BOC); 1.50 to 2.05 (Adamantyl); 1.95 (CH$_2$ in position 5') 2.83 (t) 3.01 (t) Ar—CH$_2$—CH$_2$—CO; 3.27 (m, CO$_2$C$\underline{H}_2$-Adam)); 3.41 (t, 4H, CH$_2$ in position 4' 6'); 3.67 (AB, =C—C$\underline{H}_2$—CH); 4.47 (t, SO$_2$NHC $\underline{H}$CH$_2$—C=); 6.47 (s, H3); 7.07 (dd, H6); 7.24 (d, H7); 7.33 (bs, H4).

Stage c: Hydrolysis

5-[3-oxo-3-[(1,4,5,6-tetrahydro-2-pyrimidinyl)
amino]propyl]-.alpha.-[[[[[(tricyclo-[2.3.1.1$^{3,7}$]dec-
1-yl)methoxy]carbonyl]amino]sulphonyl]amino]-2-
benzofuranpropanoic acid The operation is carried out as in Example 5 Stage c starting from 220 mg of the terbutyl ester obtained in the previous stage and 1.5 ml of trifluoroacetic anhydride. 210 mg of expected product is obtained NMR (DMSO $d_6$) 1.43 to 1.91 (Adamantyl); 2.77 (t, J=7.5) 2.96 (t, J=7.5) Ar—CH$_2$—CH$_2$—CO; 3.39 (d) 3.47 (d, $J_{AB}$=10.5) CO$_2$CH$_2$—C; 1.86 (m, CH2 in position 5'); 3.36 (1, 4H, CH$_2$ in position 4' 6'); 9.32 (s, NH); 6.58 (s, H3); 7.40 (d, J=1.5 H4); 7.11 (dd, J=1.5–8.5 H6); 7.38 (d, J=8.5 H7); 8.24 (d, J=8.5 NH); 4.31 (td, J=8.5–15.5 SO$_2$NHC HCH$_2$—C=); 3.09 (dd, J=8.5-15.5) 3.20 (dd, J=8.5–15.5) SO$_2$NHCHCH$_2$—C=.

Example 7

5-[3-oxo-3-[(1,4,5,6-tetrahydro-2-pyrimidinyl) amino]-propyl]-.alpha.-[[[[(phenyl)methoxy] carbonyl]-amino]-sulphonyl]amino]-2-benzofuranpropanoic acid

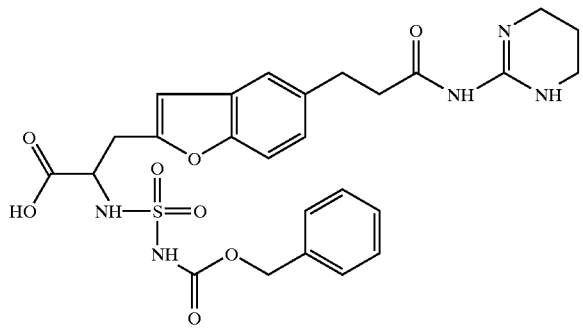

The operation is carried out as in Example 6 Stages a, b and c but, as regards Stage a, starting from benzyl alcohol instead of tricyclo[3.3.1.1$^{3,7}$]decane-1-methanol.

NMR (CDCl$_3$) 1.84 (m, CH$_2$ in position 5'); 2.75 (t) 2.94 (t, Ar—CH$_2$—CH$_2$—C=O); 3.07 (dd) 3.20 (dd) =C—C H$_2$—CH—NHSO$_2$; 4.31 (m, =C—CH$_2$—CH—NHSO$_2$); 4.87 (s, CO$_2$CH$_2$Ph); 6.59 (s, H3); 7.10 (dd, H6); 8.43 (d, H7); 7.29 to 7.43 (Benzyl, H4); 9.19 (bs, 2H) 11.30 (s, 1H) 11.82 (s, 1H) mobile H's.

Example 8

Mono(trifluoroacetate) of

.alpha.-[[[(phenylmethyl)-amino]sulphonyl]amino]-5-[3-oxo-3-[(1,4,5,6-tetrahydro-2-pyrimidinyl) amino]propyl]-2-benzofuranpropanoic acid

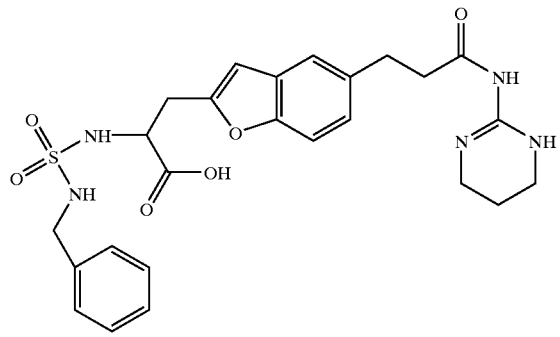

Stage a: Addition of chorosulphonyl 1,1-dimethylethyl.alpha.-[[[[(1,1-dimethylethoxy) carbonyl]amino]sulphonyl]-amino]-5-(3-methoxy-3-oxopropyl)-2-benzofuranpropanoate 131 mg of terbutyl alcohol in 5 ml of dichloromethane is added to a solution of 158 μl of chlorosulphonyl isocyanate in 5 ml of dichloromethane and the reaction medium is agitated at 0° C. for 1 hour thirty minutes. Then 692 mg of P2 amine then 490 μl of TEA are added. After washing then drying, the reaction medium is evaporated under reduced pressure and purified by chromatography eluting with a dichloromethane/acetone mixture 95/5. After purification 630 mg of expected product is obtained IR (CHCl$_3$) NH 3395 cm$^{-1}$; C=O 1736 cm$^{-1}$; conjugated system+aromatic 1600 cm$^{-1}$.

Stage b: Alkylation of the amine 1,1-dimethylethyl.alpha.-[[[[(1,1-dimethylethoxy) carbonyl](phenylmethyl)-amino]sulphonyl]amino]-5-(3-methoxy-3-oxopropyl)-2-benzofuranpropanoate 630 mg of the sulphonylurea obtained in the previous stage in 8 ml of dichloromethane is mixed at ambient temperature for 30 minutes with 185 μl of benzyl alcohol and 736 mg of betaine: ((T-4)-[(3,3-dimethyl)-1,2,5-thiadiazolidinekappa.N5)1,1-dioxidato(2-)]triphenyl-phosphorus), prepared according to J. Org. Chem (1994) 59, 2289 then after washing, drying and evaporation under reduced pressure purification is carried out by chromatography eluting with a dichloromethane/acetone mixture 95/5. 310 mg of expected product is obtained IR (CHCl$_3$) NH 3320 cm$^{-1}$; C=O 1732 cm$^{-1}$; C=C+ aromatic 1602, 1496 cm$^{-1}$.

Stage c: Formation of the acylguanidine 1,1-dimethylethyl.alpha.-[[[[(1,1-dimethylethoxy) carbonyl](phenylmethyl)-amino]sulphonyl]amino]-5-[3-oxo-3-[(1,4,5,6-tetrahydro-2-pyrimidinyl) amino]propyl]-2-benzofuranpropanoate The operation is carried out as in Example 1 but starting from the ester prepared in the previous stage and 4 equivalents of 1,4,5,6-tetrahydro-2-pyrimidinamine. 220 mg of expected product is obtained.

NMR (CDCl$_3$) 1.39 (s) 1.47 (s) 2 BOC; 1.95 (m, CH$_2$ in position 5'); 3.40 (m, CH$_2$ in position 4' and 6'); 2.85 (t) 3.01 (t) Ar—CH$_2$—CH$_2$—CO; 3.13 (m, =C—C H$_2$—CH—NHCO); 3.81 (m, =C—CH$_2$—CH—NHCO); 6.04 (m, =C—CH$_2$—CH—NHCO); 4.73 (d, J=15.5) 4.94 (d, J=15.5) X—CH$_2$—Ph; 6.43 (s, H3); 7.10 (dd, H6); 7.20 to 7.40 (m, aromatic 7H).

Stage d: Hydrolysis Then Deprotection Mono (trifluoroacetate) of

.alpha.-[[[(phenylmethyl)-amino]sulphonyl]amino]-5-[3-oxo-3-[(1,4,5,6-tetrahydro-2-pyrimidinyl) amino]propyl]-2-benzofuranpropanoic acid The operation is carried out as in Example 5 Stage c starting from 306 mg of the tert-butyl ester obtained in the previous stage and 2 ml of trifluoroacetic acid. 250 mg of expected product is obtained.

NMR (DMSO $d_6$) 1.84 (m, CH$_2$ in position 5'); 3.34 (m, CH$_2$ in position 4' and 6'), 2.77 (t) 2.95 (t) Ar—CH$_2$CH$_2$—CO; 3.04 (dd) 3.17 (dd) =C—CH$_2$—CH—NHSO2; 4.12 (m, =C—CH$_2$—CH—NHSO$_2$); 7.59 (d, =C—CH$_2$—CH—NHSO$_2$); 3.67 (dd) 3.83 (dd) Ph—CH$_2$—NH; 7.40 (masked, Ph—CH$_2$—NH); 6.64 (s, H3); 7.11 (m, aromatic 3H); 7.23 (m, aromatic 3H); 7.40 (m, aromatic 2H); 8.98 (s, mobile 2H's); 11.53 (s, mobile 1H's); 12.90 (broad, mobile 1H)

Example 9

.alpha.-[[[4-(1,1-dimethylethyl)phenyl]sulphonyl] amino]-5-(3-oxo-3-[(1,4,5,6-tetrahydro-2-pyrimidinyl)amino]propyl]-2-benzofuranpropanoic acid

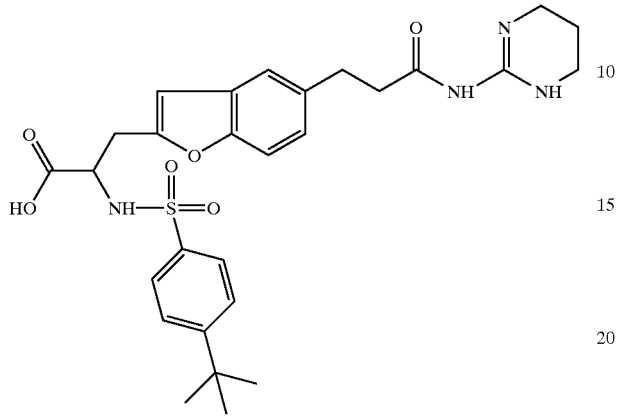

Stage a 1,1-dimethylethyl.alpha.-[[4-(1,1-dimethylethyl) phenylsuiphonyl]amino]-5-(3-methoxy-3-oxopropyl)-2-benzofuranpropanoate 24 mg of 4-dimethylaminopyridine and 466 mg of 4-tert-butyl-benzosulphonyl chloride are added under nitrogen to 347 mg of P2 in 3 ml of pyridine, and the reaction medium is agitated for 16 hours under reflux. After cooling, the reaction medium is then poured into 10 ml of water followed by extracting with dichloromethane, washing, drying and evaporating under reduced pressure until 590 mg is obtained which is purified by chromatography eluting with a cyclohexane/ethyl acetate mixture 7/3. 500 mg of pure expected product is obtained. Rf cyclohexane/ethyl acetate 7/3=0.31.

IR (CHCl$_3$) NH 3340 cm$^{-1}$; C=O 1733 cm$^{-1}$; aromatic C=C 1597 cm$^{-1}$; SO$_2$ 1348, 1156 cm$^{-1}$.

Stage b: Formation of the acyl guanidine 1,1-dimethylethyl.alpha.-[[[4-(1,1-dimethylethyl) phenylsulphonyl]amino]-5-(3-oxo-3-[(1,4,5,6-tetrahydro-2-pyrimidinyl)amino]propyl]-2-benzofuranpropanoate 500 mg of the ester prepared in the previous stage in 4 ml of THF and 200 mg of 1,4,5,6-tetrahydro-2-pyrimidinamine are mixed together for 3 hours at ambient temperature. Then the reaction medium is evaporated under reduced pressure in order to obtain 600 mg of crude product which is purified by chromatography eluting with a solvent A/ethyl acetate mixture 1/1. 312 mg of expected purified product is obtained.

IR (CHCl$_3$) complex NH 3269 cm$^{-1}$; C=O 1731, 1689 cm$^{-1}$; conjuguated system+aromatic 1663, 1597, 1576, 1496 cm$^{-1}$; SO$_2$ 1349, 1155 cm$^{-1}$.

Stage c: hydrolysis

.alpha.-[[[4-(1,1-dimethylethyl)phenyl]sulphonyl] amino]-5-(3-oxo-3-[(1,4,5,6-tetrahydro-2-pyrimidinyl)amino]propyl]-2-benzofuranpropanoic acid 3 ml of trifluoroacetic anhydride is added to 305 mg of acylguanidine prepared in the previous stage in 3 ml of dichloromethane, the reaction medium is agitated at ambient temperature for 3 hours then evaporated under reduced pressure, while adding toluene, until 300 mg of crude product is obtained in the form of a trifluoroacetic acid salt. The solution is purified by chromatography eluting with a A solvent/AcOEt 1.5:0.5. The obtained residue is taken up in 10 ml of water, CH$_2$Cl$_2$/TFA: 1/1 is mixed then the solution is evaporated under reduced pressure, taken up in toluene and reconcentrated to dryness. 254 mg of expected product is obtained.

NMR (CDCl$_3$)

1.29 (s, Ph-tBu); 1.88 (m, CH$_2$ in 5'); 3.33 (m, CH$_2$ in position 4' and 6'), 2.76 (m) 2.98 (m) Ar—CH$_2$CH$_2$—CO; 3.21 (dd, =C—CH$_2$—CH—NH); 4.30 (m, =C—CH$_2$—CH—NH); 5.20 (m, mobile 2H); 5.73 (m, mobile 1H); 6.37 (bs, H3); 6.99 (bd) 7.20 (m), H4 H6 H7; 7.39 and 7.70 (AA'BB', phenyl); 9.82 (broad s, mobile 2H's); 12.64 (s, mobile 1H)

Example 10

.alpha.-[[[4-(1-methylethyl)phenyl]sulphonyl] amino]-5-(3-oxo-3-[(1,4,5,6-tetrahydro-2-pyrimidinyl)amino]propyl]-2-benzofuranpropanoic acid

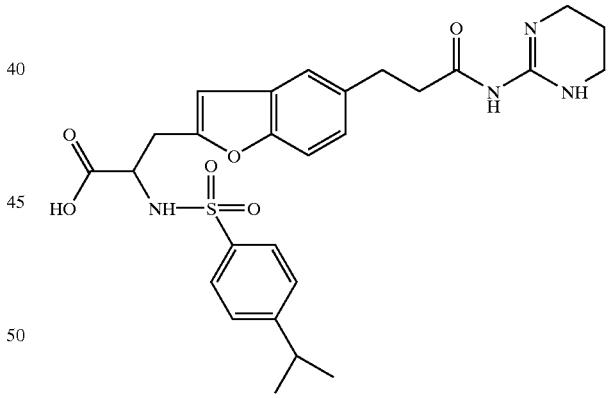

The operation is carried out as in Example 9 but starting from 4-isopropyl-benzosulphonyl chloride.

NMR (CDCl$_3$) 1.22 (d, (CH$_3$)$_2$CH) 2.90 (m, (CH$_3$)$_2$CH); (s, Ph-tBu); 1.88 (m, CH$_2$ in position 5'); 3.33 (m, CH$_2$ in position 4' and 6'), 2.77 2.98 Ar—CH$_2$CH$_2$—CO; 3.19 (=C—CH$_2$—CH—NHSO$_2$); 6.37 (s, H3); 6.99 (d, 1H benzofurane); 7.18 (2H, benzofurane); 7.21 and 7.68 (phenyl); 9.84 (NH$_2^+$ coupled to 3.33); 12.67 (s, mobile 1H).

Example 11

5-[3-oxo-3-[(1,4,5,6-tetrahydro-2-pyrimidinyl)amino]-propyl]-.alpha.-[propylsulphonyl)amino]-2-benzofuran-propanoic acid

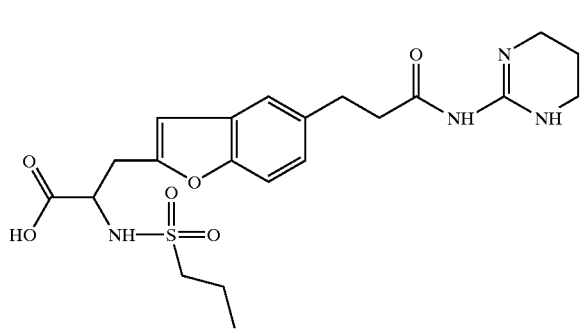

The operation is carried out as in Example 9 but starting from 4-n-propyl-benzosulphonyl chloride.

NMR (DMSO d$_6$) 0.67 (t) 1.47 (m) 2.75 (m) CH$_3$—CH$_2$—CH$_2$—SO$_2$; 1.85 (m, CH$_2$ in position 5'); 2.50 (masked, =N—CH$_2$—CH$_2$); 3.35 (m, CH$_2$ in position 4' and 6'), 2.75, 2.95(m, 4H Ar—CH$_2$CH$_2$—CO); 4.23 (m, =C—CH$_2$—CH—NHSO$_2$); 6.64 (s, H3); 7.12 (d, 1H H7); 7.42 (m, 2H, H4 and H6); 9.29 (bs, mobile 2H); 11.96 (s, mobile 1H); 13.14 (b, mobile 1H).

Example 12

.alpha.-[methylsulphonyl)amino]-5-[3-oxo-3-[(1,4,5,6-tetrahydro-2-pyrimidinyl)amino]propyl]-2-benzofuranpropanoic acid

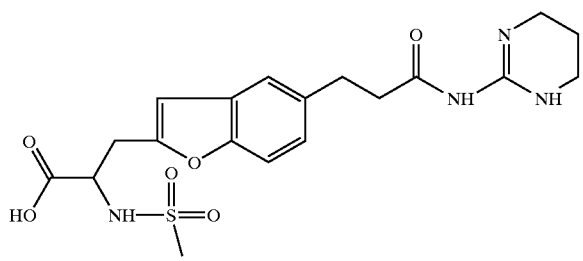

The operation is carried out as in Example 9 but starting from 4-methyl-benzosulphonyl chloride.

NMR (CDCl$_3$) 1.85 (m, CH$_2$ in position 5'); 2.50 (masked, =N—CH$_2$—CH$_2$); 3.35 (m, CH$_2$ in position 4' and 6'), 2.75 (t) 2.95 (t) Ar—CH$_2$CH$_2$—CO; 2.90 (m, 2H, SO$_2$CH$_3$); 3.09 (dd) 3.24 (dd) =C—CH$_2$—CH—NHSO$_2$; 4.28 (m, =C—CH$_2$—CH—NHSO$_2$); 7.79 (d, =C—CH$_2$—CH—NHSO$_2$) 6.64 (s, H3); 7.12 (d, 1H H7); 7.42 (m, 2H, H4 and H6); 9.30 (s) 11.96 (s) 13.14 (1), mobile H's.

Example 13

.alpha.-[(1-naphthalenylsulphonyl)amino]-5-[3-oxo-3-[(1,4,5,6-tetrahydro-2-pyrimidinyl)amino]propyl]-2-benzofuranpropanoic acid.

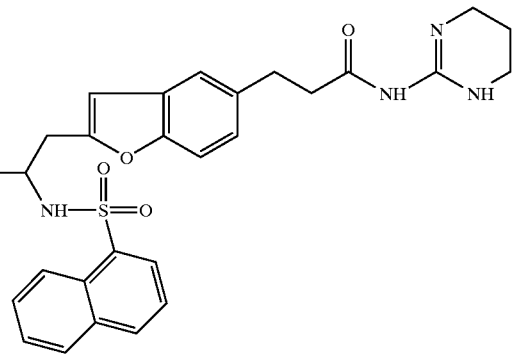

The operation is carried out as in Example 9 but starting from sulphonyl-1-naphthalene chloride

Example 14

1-methylethyl alpha.-[(1-naphthalenylsulphonyl)amino]-5-[3-oxo-3-[(1,4,5,6-tetrahydro-2-pyrimidinyl)amino]propyl]-2-benzofuranpropanoate

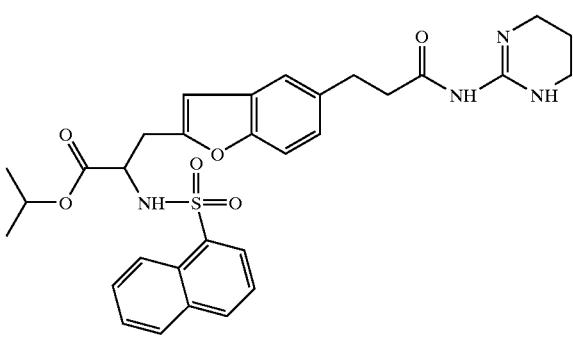

The operation is carried out as in Example 2 starting from 648 mg of acid prepared in Example 13 and 20 ml of isopropanol. 350 mg of expected product is obtained.

NMR (CDCl$_3$) 0.98 (d, (CH$_3$)$_2$CH); 4.77 (m, (CH$_3$)$_2$CH); 2.02 (m, CH$_2$ in position 5'); 3.48 (m, CH$_2$ in position 4' and 6'), 2.89 (t) 3.06 (t) Ar—CH$_2$CH$_2$—CO; 3.05 (dd) 3.15 (dd) =C—CH$_2$—CH—NHSO2; 4.28 (m, =C—CH$_2$—CH—NHSO2); 5.70 (d, =C—CH$_2$—CH—NHSO$_2$) 6.35 (s, H3); 7.0 to 7.20 (3H, benzofurane); 7.44 (t, naphthalene H3); 8.00 (d) and 8.21 (d) naphthalene H2 and H4; 7.57 (m, naphthalene H6 and H7); 7.87 8.56 (naphthalene H5 and H8); 9.40 (bs, mobile 2H) 12.84 (s, mobile 1H)

Pharmacological Test

Kistrin/Vitronectin Receptor ($\alpha_v\beta_3$) ELISA Test Protocol 96-well MaxiSorp plates are coated overnight at 40 C. with 100 µl of Kistrin at 1 µg/ml (dilution in coating buffer: 0.05M (carbonate)/NaOH pH 9.6. The next day, the wells are emptied and the ligands (kistrin) are then fixed (fixation buffers: PBS containing 0.5% BSA (pH=7.4)) for 1 hour at ambient temperature under gentle agitation of 125 rpm. The wells are washed six times (washing buffer: PBS containing 0.05% Tween 20 (pH 7.7) then the following is added per well and in this order:

40 µl of incubation buffer

10 µl of the dilution of the product to be tested (the products are diluted in a 50:50 DMSO/water mixture)

50 µl of human $\alpha_v\beta_3$ receptor (cf Pytel et al. Methods Enzymol. (1987) 144 (Dilution in incubation buffer, adapted according to the batch of receptor and according to the ligand). The ligand, the $\alpha_v\beta_3$ receptor and the products to be studied are incubated for 3 hours at ambient temperature with gentle agitation of 125 rpm.

The wells are again washed six times, then incubated for 2 hours at ambient temperature with gentle agitation of 125 rpm, in the presence of 100 µl of anti-receptor antibody coupled to a peroxidase (The 4B12-HRP antibody is diluted in incubation buffer (50 mM TRIS pH 7.4; 0.5% BSA; 0.05% Tween 20; 1 mM $MnCl_2$; 50 µM $CaCl_2$; 50 µM $MgCl_2$; 100 mM NaCl). The dilution is to be adapted according to the batch of receptor.

The wells are then washed six times before measurement of the ligand-receptor bond is carried out using a peroxidase developer kit (TBM Microwell Peroxidase Substrate System Kirkegaard; Ref cat 50-76-00).

This kit contains a flask A of substrate (3,3',5,5'-tetramethylebenzidine at 0.4 g/l) and a flask B ($H_2O_2$ to 0.02% in Citrate/Citric acid). Extemporaneously, one volume of A is mixed with one volume of B, then the reaction mixture is distributed at a rate of 100 µl/wells.

The enzymatic reaction develops between 6 to 10 minutes for Kistrin/$\alpha_v\beta_3$ then its development is stopped by the addition of 100 µl of 1M phosphoric acid. The optical density is determined at 450 nm.

Expression of the Results

The following curve is plotted: the bond percentage as a function of the logarithm of each concentration of the tested product.

For each product IC50 is determined according to the following formula: IC50=(B0+Bmin)/2

B0=Maximum bond in the absence of any product
Bmin=Minimum bond in the presence of the highest concentration of the product.

| Example | K/VnR $IC_{50}$ (µM) |
|---------|---------------------|
| 1       | 0.009               |
| 5       | 0.045               |
| 7       | 0.01                |
| 6       | 0.065               |
| 8       | 0.0087              |
| 13      | 0.0055              |
| 14      | 3.7                 |
| 9       | 0.015               |
| 10      | 0.0091              |
| 11      | 0.0057              |
| 12      | 0.0067              |

What is claimed is:
1. A compound of formula (I)

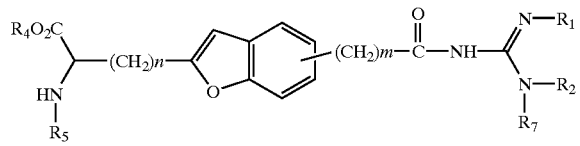

in which
either $R_1$ and $R_2$, independently from one another represent a hydrogen atom or an alkyl group containing from 1 to 6 carbon atoms non-substituted or substituted by $R_3$,
or $R_1$ and $R_2$ together form a divalent alkylene radical containing 2 to 9 carbon atoms, saturated or unsaturated, such as —$(CH_2)_p$— in which p is 2, 3, 4, 5, 6, 7, 8 or 9, non-substituted or substituted by one or more radicals chosen from halogen, ($C_1$–$C_6$)-alkyl, ($C_1$–$C_6$)-alkoxy, ($C_6$–$C_{14}$)-aryl, ($C_6$–$C_{14}$)-aryl-($C_1$–$C_6$)-alkyl, ($C_5$–$C_{14}$)-heteroaryl, ($C_5$–$C_{14}$)-heteroaryl-($C_1$–$C_6$)-alkyl, ($C_3$–$C_{12}$)-cycloalkyl ($C_3$–$C_{12}$)-cycloalkyl-($C_1$–$C_6$)-alkyl and oxo, said divalent alkylene radical being able to be attached at the level of the carbon-carbon bond to a carbocycle or a heterocycle with 5 to 7 members, containing 1 or 2 nitrogen atoms, saturated or unsaturated, non-substituted or substituted by 1 or 2 R3 radicals;
$R_3$ represents a ($C_1$–$C_8$)-alkyl, ($C_1$–$C_8$)-alkoxy, ($C_5$–$C_{14}$)-aryl, ($C_5$–$C_{14}$)-aryl-($C_1$–$C_4$)-alkyl, halogen, trifluoromethyl, hydroxyl, nitro, amino, NH—(($C_1$–$C_4$)-alkyl), N(($C_1$–$C_4$)alkyl)$_2$, NHCO—($C_1$–$C_4$)-alkyl or CO—($C_1$–$C_4$)alkyl group;
$R_4$ represents
either a hydrogen atom, or a ($C_1$–$C_6$)-alkyl-CO—O—($C_1$–$C_4$)-alkyl or ($C_1$–$C_6$)-alkyl group, non-substituted or substituted by a radical chosen from hydroxyl, ($C_1$–$C_4$)-alkoxy, ($C_1$–$C_4$)-alkyl-$SO_2$, $NR_9R_9'$ and $N^+R_9R_9'R_9''Q^-$, in which $R_9$, $R_9'$ and $R_9''$ independently from one another, represent a hydrogen, a ($C_1$–$C_6$)-alkyl, ($C_5$–$C_{14}$)-aryl or ($C_5$–$C_{14}$)-aryl-($C_1$–$C_6$)-alkyl group and $Q^-$ is a physiologically acceptable anion,
or one of the following radicals:

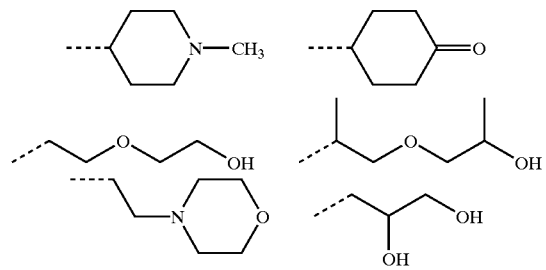

the dotted lines representing the position of the bond;
$R_5$ represents a hydrogen atom or a group chosen from $COR_6$, $CO_2R_6$, $SO_2R_6$, $SO_2NHR_6$, $SO_2NHCOR_6$, $SO_2NHCO_2R_6$, $CONH_2$ and $CONHR_6$ in which $R_6$ represents ($C_1$–$C_8$)-alkyl, ($C_6$–$C_{14}$)-aryl, ($C_6$–$C_{14}$)-aryl-($C_1$–$C_6$)-alkyl, ($C_5$–$C_{14}$)-heteroaryl or ($C_5$–$C_{14}$)-heteroaryl-($C_1$–$C_6$)-alkyl, ($C_3$–$C_{20}$) (mono-, bi- or tri-)-cycloalkyl, ($C_3$–$C_{20}$) (mono-, bi- or tri-)-cycloalkyl-($C_1$–$C_6$)alkyl, the aryl or heteroaryl radical being non-substituted or substituted by 1, 2 or 3 R3 radicals;

$R_7$ represents a hydrogen atom, $(C_1-C_6)$-alkyl-O—CO—, hydroxyl, $(C_1-C_6)$-alkyl-O—CO—O or nitro;

m is equal to 0, 1, 2 or 3;

n is an integer equal to 1, 2 or 3;

said compounds of formula (I) being in all their possible isomer forms, alone or in a mixture in any ratio, the acylguanidine group adjacent to the phenyl being in para or meta position of the oxygen, as well as their physiologically acceptable salts and their promedicaments (prodrugs).

2. A compound of claim 1 having the formula

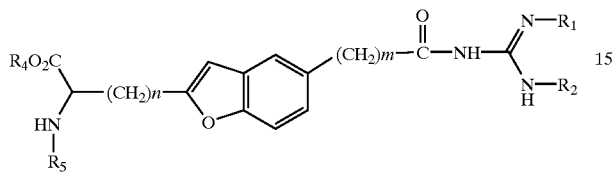

wherein $R_1$ and $R_2$ are hydrogen or together form a saturated or unsaturated divalent alkylene of 2 to 5 carbon atoms, said alkylene being unsubstituted or substituted by one or two members of the group consisting of halogen, $C_1-C_6$)-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, said alkylene to be attached at the level of the carbon-carbon bond to a carbocycle or a heterocycle containing 1 or 2 nitrogen atoms, with 5 to 7 ring members, saturated or unsaturated, unsubstituted or substituted by 1 or 2 $R_3$;

$R_3$ is alkyl or alkoxy of 1 to 6 carbon atoms;

$R_4$ is hydrogen or alkyl of 1 to 6 carbon atoms unsubstituted or substituted by a member of the group consisting of $(C_1-C_4)$-alkoxy, $(C_1-C_4)$-alkyl-$SO_2$— and —$NR_9R_9'$, $R_9$ and $R_9'$ are independently hydrogen or $(C_1-C_4)$-alkyl, $R_5$ is a member selected from the group consisting hydrogen, —$CO_2R_6$, —$SO_2R_6$, —$SO_2R_6$, —$SO_2NHR_6$ and —$SO_2NHCO_2R_6$, $R_6$ is a member selected from the group consisting of $(C_1-C_6)$-alkyl, naphthyl, unsubstituted or unsubstituted by $R_3$, cycloalkyl of 3 to 12 carbon atoms, $(C_3-C_{12})$-cycloalkyl-$(C_1-C_6)$-alkyl and the radical of formula II

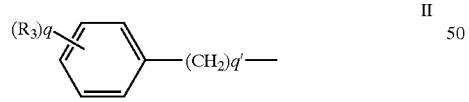

in which $R_3$ can be different, and can be situated at any position on the phenyl, q and q' are 0 or 1;

m is an integer of 1, 2 or 3;

n is an integer of 1, 2 or 3;

said compounds of formula I being in all their possible isomer forms, alone or in a mixture in any ratio, as well as its pharmaceutically acceptable salts and its prodrugs.

3. A compound of formula (I') as defined in claim 2 in which, $R_1$ and $R_2$ represent a hydrogen atom, or together form a saturated or unsaturated divalent alkylene radical containing 2 to 4 carbon atoms or more particularly represent a hydrogen atom or together form a —$(CH_2)_p$— group, in which p is 2, 3 or 4, said alkylene radical or —$(CH_2)_p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, said alkylene or —$(CH_2)_p$— group being able to be attached at the level of the carbon-carbon bond to a carbocycle or a heterocycle containing 1 or 2 nitrogen atoms, with 5 to 7 members, saturated or unsaturated, non-substituted or substituted by $R_3$ and in particular by 1 or 2 R3 radicals;

$R_3$ represents an alkyl or alkyloxy group containing 1 to 6 carbon atoms;

$R_4$ represents a hydrogen atom or an alkyl group containing 1 to 6 carbon atoms;

$R_5$ represents a hydrogen atom, a $CO_2R_6$, $SO_2R_6$, $SO_2NHR_6$ or $SO_2NHCO_2R_6$ group in which $R_6$ is a $(C_1-C_8)$-alkyl or naphthyl radical, non-substituted or substituted by $R_3$, a cycloalkyl radical containing 3 to 12 carbon atoms or $(C_3-C_{12})$-cycloalkyl-$(C_1-C_6)$alkyl or the radical of formula (II)

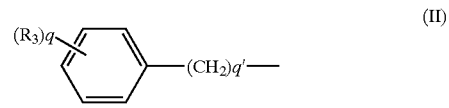

in which the $R_3$ radicals can be identical or different, and can be situated at any position of the phenyl radical, q and q' are equal to 0 or 1;

m is an integer equal to 1, 2 or 3;

n is an integer equal to 1, 2 or 3;

said compounds of formula (I) being in all their possible isomer forms, alone or in a mixture in any ratio, as well as their physiologically acceptable salts and their prodrugs.

4. A compound of formula (I') of claim 2 wherein $R_1$ and $R_2$ are hydrogen, or together form a saturated or unsaturated divalent alkylene of 2 to 3 carbon atoms, said alkylene radical being non-substituted or substituted by one or two members of the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$alkyl, $(C_5-C_{14})$-heteroaryl, $(C_5-C_{14})$-heteroaryl-$(C_1-C_6)$-alkyl, $(C_3-C_{12})$-cycloalkyl, $(C_3-C_{12})$-cycloalkyl-$(C_1-C_6)$-alkyl and oxo, said alkylene being able to be attached at the level of the carbon-carbon bond to a carbocycle or a heterocycle containing 1 or 2 nitrogen atoms, with 5 to 7 ring members, saturated or unsaturated, non-substituted or substituted by $R_3$;

$R_3$ is alkyl or alkoxy of 1 to 6 carbon atoms;

$R_4$ is hydrogen or alkyl of 1 to 6 carbon atoms;

$R_5$ is selected from the group consisting of hydrogen, —$CO_2R_6$, —$SO_2R_6$, —$SO_2NHR_6$, and —$SO_2NHCO_2R_6$, $R_6$ is selected from the group consisting of $(C_1-C_8)$-alkyl, naphthyl non-substituted or substituted by $R_3$, cycloalkyl of 3 to 12 carbon atoms, $(C_3-C_{12})$-cycloalkyl-$(C_1-C_6)$-alkyl and

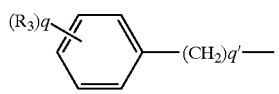

wherein $R_3$s can be identical or different, and can be situated at any position of the phenyl, q and q' are 0 or 1;

m is 2;

n is 1;

said compounds of formula (I) being in all their possible isomer forms, alone or in a mixture in any ratio, and their pharmaceutically acceptable salts and their prodrugs.

5. A compound of formula (I) of claim 1 wherein $R_5$ is —$CO_2R_6$, $R_6$ is as defined in claim 1, said compound of formula (I) being in all their possible isomer forms, alone or in a mixture in any ratio, as well as their pharmaceutically acceptable salts and their prodrugs.

6. A compound of formula (I) of claim 1 wherein $R_5$ is —$SO_2R_6$, $R_6$ is as defined in claim 1, naphthyl and phenyl substituted by at least one alkyl of 1 to 6 carbon atoms, or $CF_3$, said compounds of formula (I) being in all their possible isomer forms, alone or in a mixture in any ratio, as well as their pharmaceutically acceptable salts and their prodrugs.

7. A compound of formula (I) of claim 1 wherein $R_5$ is —$SO_2NHR_6$ or —$SO_2NHCO_2R_6$, $R_6$ is as defined in claim 1, said compounds of formula (I) being in all their possible isomer forms, alone or in a mixture in any ratio, as well as their pharmaceutically acceptable salts and their prodrugs.

8. A compound of formula (I) of claim 1 selected from the group consisting of

5-[3-oxo-3-[(1,4,5,6-tetrahydro-2-pyrimidinyl)amino-propyl]-.alpha.-[[(phenylmethoxy)carbonyl]amino]-2-benzofuranepropanoic acid, 1-methylethyl 5-[3-oxo-3-[(1,4,5,6-tetrahydro-2-pyrimidinyl)amino]-propyl-.alpha.-[[(phenylmethoxy)carbonyl]amino]-2-benzo-furanpropanoate, ethyl 5-[3-oxo-3-[(1,4,5,6-tetrahydro-2-pyrimidinyl) amino]-propyl]-.alpha.-[[(phenylmethoxy)carbonyl]amino]-2-benzofuranpropanoate, 5-[3-oxo-3-[(1,4,5,6-tetrahydro-2-pyrimidinyl)amino] propyl]-.alpha.[[[(tricyclo-[3.3.1.1$^{3,7}$]dec-1-yl)methoxy]-carbonyl]amino]-2-benzofuranpropanoic, 5-[3-oxo-3-[(1,4,5,6-tetrahydro-2-pyrimidinyl)-amino] propyl]-.alpha.-[[[[(tricyclo[2.3.1.1$^{3,7}$]dec-1-yl)-methoxy]carbonyl]amino]sulphonyl]amino]-2-benzofuranpropanoic acid, 5-[3-oxo-3-[(1,4,5,6-tetrahydro-2-pyrimidinyl)amino] propyl]-.alpha.-[[[[(phenyl)methoxy]carbonyl]-amino] sulphonyl]amino]-2-benzofuranpropanoic acid, .alpha.-[[[(phenylmethyl)-amino]sulphonyl]amino]-5-[3-oxo-3-[(1,4,5,6-tetrahydro-2-pyrimidinyl)amino]propyl]-2-benzofuranpropanoic, .alpha.-[[[4-(1,1-dimethylethyl)phenyl]sulphonyl]-amino]-5-(3-oxo-3-[(1,4,5,6-tetrahydro-2-pyrimidinyl)-amino]-propyl]-2-benzofuranpropanoic acid, .alpha.-[[[4-(1-methylethyl)phenyl]sulphonyl]amino]-5-(3-oxo-3-[(1,4,5,6-tetrahydro-2-pyrimidinyl)amino]propyl]-2-benzofuranpropanoic acid, 5-[3-oxo-3-[(1,4,5,6-tetrahydro-2-pyrimidinyl)-amino] propyl]-.alpha.-[propylsulphonyl)amino]-2-benzofuranpropanoic acid, .alpha.-[methylsulphonyl)amino]-5-[3-oxo-3-[(1,4,5,6-tetrahydro-2-pyrimidinyl)amino]propyl]-2-benzofuranpropanoic acid, .alpha.-[(1-naphthalenylsulphonyl)amino]-5-[3-oxo-3-[(1,4,5,6-tetrahydro-2-pyrimidinyl)amino]propyl]-2-benzofuranpropanoic acid, 1-methylethyl alpha.-[(1-naphthalenylsulphonyl)amino]-5-[3-oxo-3-[(1,4,5,6-tetrahydro-2-pyrimidinyl)amino] propyl]-2-benzofuranpropanoate and their pharmaceutically acceptable salts and their prodrugs.

9. A process for the preparation of a compound of formula (I) of claim 1 comprising coupling of at least two fragments which can be derived by retrosynthesis from the compounds of formula (I).

10. The process of claim 9 comprising forming a carboxylic acid of the formula

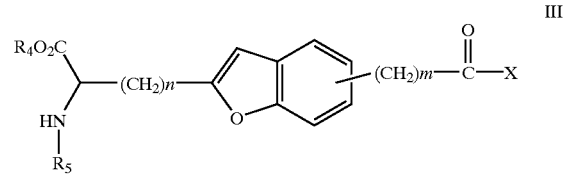

wherein $R_4$, $R_5$, n and m are as defined in claim 1 and X is a parting group which can be substituted by a nucleophile, by reaction in the presence of a catalyst and in basic medium of an amino ester of the formula

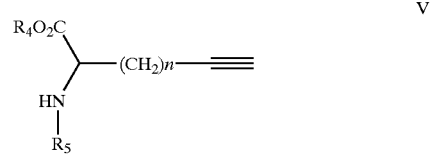

wherein $R_4$, $R_5$ and n are as defined in claim 1 with a carboxylic acid of the formula

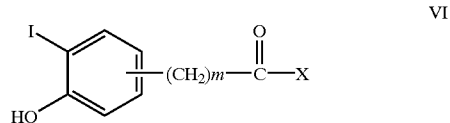

wherein m and X are as defined above, the functional groups optionally present in the form of precursors or in protected form, being subsequently converted to groups present in the compounds of formula (I) and coupling of the carboxylic acid of formula (III) with a guanidine of the formula

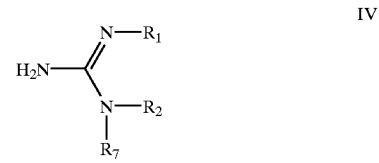

wherein $R_1$, $R_2$ and $R_7$, are as defined in claim 1, the functional groups optionally present in the form of precursors or in protected form being subsequently converted to groups present in the compounds of formula (I).

11. A composition for treating osteoporosis comprising an amount of a compound of claim 1 sufficient to treat osteoporosis and an inert pharmaceutical carrier.

12. An anti-inflammatory composition comprising an anti-inflammatorily effective amount of a compound of claim 1 and an inert pharmaceutical carrier.

13. A method of treating osteoporosis in warm-blooded animals comprising administering to warm-blooded animals in need thereof an amount of a compound of claim 1 sufficient to treat osteoporosis.

14. A method of treating cardiovascular disorders in warm-blooded animals comprising administering to warm-blooded animals in need thereof an amount of a compound of claim 1 sufficient to treat cardiovascular disorders.

* * * * *